(12) United States Patent
Rovani, Jr. et al.

(10) Patent No.: US 10,449,502 B2
(45) Date of Patent: *Oct. 22, 2019

(54) METHODS FOR ANALYZING HYDROCARBONS AND HYDROCARBON BLENDS FOR CHEMICAL COMPOSITIONS

(71) Applicant: The University of Wyoming Research Center, Laramie, WY (US)

(72) Inventors: Joseph F. Rovani, Jr., Laramie, WY (US); Jean-Pascal Planche, Laramie, WY (US); Ryan Bradley Boysen, Laramie, WY (US)

(73) Assignee: The University of Wyoming Research Corporateion, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,584

(22) Filed: Nov. 7, 2018

(65) Prior Publication Data

US 2019/0091642 A1    Mar. 28, 2019

Related U.S. Application Data

(63) Continuation-in-part of application No. 15/358,991, filed on Nov. 22, 2016, which is a continuation of
(Continued)

(51) Int. Cl.
*B01F 17/00* (2006.01)
*C08L 95/00* (2006.01)
(Continued)

(52) U.S. Cl.
CPC ...... *B01F 17/0085* (2013.01); *B01F 17/0014* (2013.01); *B01F 17/0078* (2013.01);
(Continued)

(58) Field of Classification Search
CPC .............. B01F 17/0014; B01F 17/0078; B01F 17/0085; C08J 2395/00; C08L 2555/10;
(Continued)

(56) References Cited

U.S. PATENT DOCUMENTS 4,493,765 A    1/1985  Long et al.
4,628,204 A    12/1986 Maes
(Continued)

FOREIGN PATENT DOCUMENTS

EP      400989 A      5/1990
WO      0077120 A2    12/2000
(Continued)

OTHER PUBLICATIONS

"Standard Test Method for Separation of Asphalt into Four Fractions1," ASTM International, Designation D4124-09.
(Continued)

*Primary Examiner* — Lyle Alexander
*Assistant Examiner* — Bryan Kilpatrick
(74) *Attorney, Agent, or Firm* — Santangelo Law Offices, PC

(57) ABSTRACT

The present invention is generally related to the analysis of chemical compositions of hydrocarbons and hydrocarbon blends. This method, in particular embodiments, may apply specifically to the problem of analyzing extremely complex hydrocarbon-containing mixtures when the number and diversity of molecules makes it extremely difficult or impossible to realistically identify and quantify them individually in a reasonable timeframe. Particular SEC (size exclusion chromatography)-based methods and apparatus disclosed herein may be used to measure, e.g., the molecular size, weight, and/or volume, whether in absolute or relative manner, of the various components of eluate from the SEC stationary phase (e.g., a permeable gel). This analytical
(Continued)

method is applicable on a wide variety of hydrocarbonaceous materials, and especially useful for, but not limited to oil, maltenes of oil, asphalt binders and asphalt binder blends, which may contain wide varieties of different types of additives, modifiers, and chemistries.

34 Claims, 12 Drawing Sheets

Related U.S. Application Data application No. 13/723,058, filed on Dec. 20, 2012, now abandoned, which is a continuation-in-part of application No. 13/600,039, filed on Aug. 30, 2012, now Pat. No. 8,492,154, which is a continuation of application No. 13/490,307, filed on Jun. 6, 2012, now Pat. No. 8,530,240, and a continuation of application No. 13/490,316, filed on Jun. 6, 2012, now Pat. No. 8,367,425, and a continuation of application No. 13/243,782, filed on Sep. 23, 2011, now Pat. No. 8,273,581, which is a continuation of application No. 12/970,535, filed on Dec. 16, 2010, now Pat. No. 8,241,920, which is a continuation of application No. 11/510,491, filed on Aug. 25, 2006, now Pat. No. 7,875,464, and a continuation-in-part of application No. PCT/US2012/021317, filed on Jan. 13, 2012, and a continuation-in-part of application No. 13/237,568, filed on Sep. 20, 2011, now Pat. No. 9,353,317.

(60) Provisional application No. 62/582,808, filed on Nov. 7, 2017, provisional application No. 61/700,090, filed on Sep. 12, 2012, provisional application No. 60/711,599, filed on Aug. 25, 2005, provisional application No. 61/450,515, filed on Mar. 8, 2011.

(51) Int. Cl.
G01N 30/02 (2006.01)
G01N 33/28 (2006.01)

(52) U.S. Cl.
CPC ......... *C08L 95/005* (2013.01); *C08J 2395/00* (2013.01); *C08L 2555/10* (2013.01); *G01N 30/02* (2013.01); *G01N 33/28* (2013.01); *Y02A 30/333* (2018.01)

(58) Field of Classification Search
CPC ..... C08L 95/005; Y02A 30/333; G01N 30/02; G01N 33/28
See application file for complete search history.

(56) References Cited

U.S. PATENT DOCUMENTS

| | | | |
|---|---|---|---|
| 4,634,680 A | 1/1987 | Kingsley | |
| 4,865,741 A | 9/1989 | Nolte | |
| 4,988,446 A | 1/1991 | Haberman | |
| 4,990,773 A | 2/1991 | Supernaw et al. | |
| 5,092,983 A | 3/1992 | Eppig et al. | |
| 5,266,800 A | 11/1993 | Mullins | |
| 5,381,002 A | 1/1995 | Morrow et al. | |
| 5,424,959 A | 6/1995 | Reyes et al. | |
| 5,574,215 A | 11/1996 | Bunger et al. | |
| 5,861,228 A | 1/1999 | Descales et al. | |
| 5,969,237 A | 10/1999 | Jones et al. | |
| 6,773,921 B1 | 8/2004 | Schabron et al. | |
| 7,875,464 B2 * | 1/2011 | Schabron | G01N 33/28 206/177 |
| 8,241,920 B2 | 8/2012 | Schabron et al. | |
| 8,273,581 B2 | 9/2012 | Schabron et al. | |
| 8,367,425 B1 | 2/2013 | Schabron et al. | |
| 8,492,154 B1 | 7/2013 | Schabron et al. | |
| 8,530,240 B1 | 9/2013 | Schabron et al. | |
| 8,628,970 B1 | 1/2014 | Schabron et al. | |
| 9,353,317 B2 | 5/2016 | Schabron et al. | |
| 9,458,389 B1 * | 10/2016 | Schabron | G01N 33/28 |
| 2003/0211621 A1 | 11/2003 | Rovani et al. | |
| 2007/0048874 A1 | 3/2007 | Schabron et al. | |
| 2011/0062058 A1 | 3/2011 | Rogel et al. | |
| 2011/0066441 A1 | 3/2011 | Orvalles et al. | |
| 2011/0120950 A1 | 5/2011 | Schabron et al. | |
| 2012/0016168 A1 | 1/2012 | Schabron et al. | |
| 2012/0160015 A1 | 6/2012 | Ovalles et al. | |

FOREIGN PATENT DOCUMENTS

| | | |
|---|---|---|
| WO | 0077120 A3 | 12/2000 |
| WO | 02063292 A1 | 8/2002 |
| WO | 03096011 A1 | 11/2003 |
| WO | 2011032123 A2 | 3/2011 |
| WO | 2011032125 A2 | 3/2011 |
| WO | 2011038125 A2 | 3/2011 |
| WO | 2011113017 A2 | 9/2011 |
| WO | 2011/127044 | 2/2012 |
| WO | WO2011/127044 | 2/2012 |

OTHER PUBLICATIONS

"Energy and Environmental Profile of the US Petroleum Refining Industry," 1988, Prepared by Energetics Inc. for U.S. Department of Energy Office of Industrial Technologies.
Schabron, J.F., et al., "Asphaltene Determinator Method for Automated On-Column Precipitation and Redissolution of Pericondensed Aromatic Asphaltene Components," Energy Fuels 2010, 24, 5984-5996, DOI: 10.102/ef100822f.
Fan, T. et al., "Rapid and Accurate SARA Analysis of Medium Gravity Crude Oils," Energy & Fuels 2002, 16, 1571-1575.
Schabron, J.F., et al., "On-column precipitation and re-dissolution of asphaltenes in petroleum residua," Fuel 87 (2008) 165-176.
Grizzle, Patrick L, et al., "Automated Liquid Chromatographic Compound Class Grou-Type Separation of Crude Oils and Bitumens Using Chemically Bonded Aminosilane," Anal. Chem. 1986, 58, 2389-2396.
Jewell, D.M. et al., "Ion-Exchange, Coordination, and Adsorption Chromatographic Separation of Heavy-End Petroleum Distillates," Laramie Energy Research Center, Analytical Chemistry, vol. 44, No. 8, Jul. 1972, p. 1391.
Jiang, C et al., "TLC-FID (Iatroscan) analysis of heavy oil and tar sand samples," Organic Geochemistry 39 (2008) 1210-1214.
Karlsen, D.A. et al., "Analysis of petroleum fractions by TLC-FID: applications to petroleum reservoir description," Org. Geochem. vol. 17, No. 5, pp. 603-617, 1991.
Kharrat, A. et al., "Issues with Comparing SARA Methodologies," Energy & Fuels 2007, 21, 3618-3621.
Masson, J-F et al., "Dynamics of Bitumen Fractions by Thin-Layer Chromatography/Flame Ionization Detection," Energy & Fuels 2001, 15, 955-960.
Radke, M et al., "Preparative Hydrocarbon Group Type Determination by Automated Medium Pressure Liquid Chromatography," Anal. Chem. 1980, 52, 406-411.
Schabron, J.F. et al.; "Petroleum Processing Efficiency Improvement," Topical Report, May 2011.
Wiehe, Irwin A. et al.; "The Oil Compatibility Model and Crude Oil Incompatibility," Energy & Fuels 2000, 14, 56-59.
Fan, Z et al.; "Challenges in Processing Bitumens and Heavy Oils," Prepr. Pap.-Am. Chem. Soc., Div. Petr. Chem. 2009, 54 (1), 4.
"Canada regulator approves Enbridge diluent Line," Reuters, Business & Financial News, Feb. 19, 2008, Calgary, Alberta.
"Opportunity Crudes Report II: Technologies and Strategies for Meeting Evolving Market and Environmental Challenges," Hydrocarbon Publishing Company, an updated and expanded study of the 2006 report titled "Opportunity Crudes: Technical Challenges and Economic Benefits."
USPTO Office Action for U.S. Appl. No. 11/510,491 dated Dec. 9, 2010.

(56) References Cited

OTHER PUBLICATIONS

USPTO Office Action for U.S. Appl. No. 11/510,491 dated Sep. 3, 2010.
USPTO Office Action for U.S. Appl. No. 11/510,491 dated Jul. 13, 2009.
USPTO Office Action for U.S. Appl. No. 11/510,491 dated Mar. 30, 2010.
USPTO Office Action for U.S. Appl. No. 11/510,491 dated Mar. 2, 2011.
http://www.specialchem4adhesives.com/resources, Determining Critical Surface Tension of Solid Substrates, printed Sep. 13, 2011, 3 pages.
Energy Information Administration/Capacity Report 2001.
Robinson, P. R., Petroleum Processing Overview, Practical Advances in Petroleum Processing 2006:1-78.
Rogel, E. et al. Asphaltene Stability in Processed Samples using Solubility Profile Analysis, Prepr. Pap.-Am. Chem. Soc. Div. Pet. Chem. 2011, 56(1), 3.
Ovalles, C. et al. Characterization and Preparative Separation of Heavy Crude Oils, their fractions and thermally Cracked Products by the Asphaltene solubility Fractions Method, Prepr. Pap.-Am. Chem. Soc. Div. Pet. Chem. 2011, 56(1), 8.
Schabron J. F. et al., Total Pericondensed Aromatic (TPA) Determination as an Alternative to Gravimetric Asphaltenes, Prepr. Pap.-Am. Chem. Soc. Div. Pet. Chem. 20011, 66(1), 38.
Rogel, E. et al. Determination of Asphaltenes in Crude Oil and Petroleum Products by the on Column Precipitation Method, Energy Fuels 2009, 23, 4515-4521.
"Energy and Environmental Profile of the US Petroleum Refining Industry," 1988, Prepared by Energetics Inc. for U.S. Department of Energy Office of Industrial Technologies, pp. 4-5, 27, 33, 49 and 62-63.
"Standard Test Method for Molecular Weight (Relative Molecular Mass) of Hydrocarbons by Thermoelectric Measurement of Vapor Pressure," ASTM Designation: D 2503-82 (Reapproved 1997), 871-873.
Andersen, S.I. et al., 1991, "Aggregation of Asphaltenes as Determined by Calorimetry," Journal of Colloid and Interface Science, 142, 497-502, 1991.
Barton, A.F., 1974, "Solubility Parameters," Chemical Reviews, 75 (6), 731-753.
Bodusynski, M.M. et al., 1982, Separation of Solvent-Refined Coal into Solvent-Derived Fractions, Analytical Chemistry, 54, 372-375.
Burrell, H., 1955, Solubility Parameters Interchemical Review, 3-16.
Carrier, H. et al; Acoustic method for measuring asphaltene flocculation in crude oil▲, Journal of Petroleum Science and Engineering, pp. 111-117.
Cartz, L., ch. 3, Ultrasonic Testin✳, Nondestructive Testing, 1995, pp. 81-98.
Del Bianco, A. et al., 1993, Thermal Cracking of Petroleum Residues 1. Kinetic Analysis of the Reaction. Fuel, 72 (1), 7✕ 80.
Heithaus, J.J., 1962, Measurement and Significance of Asphaltene Peptization✎ Journal of the Institute of Petroleum 48 (458), 45-53.
Hildebrand, J.H. et al., 1970, Regular and Related Solutions § Van Nostrand Reinhold, NY, pp. 24-27, pp. 152-153, pp. 212-215.
Jones et al. Development of an ultrasonic oil stability monitor for the assessment of asphaltene aggregation in hydrocarbon stream▲, Proceed. Intern. Conf. Mitigat. Heat Exch. Foul. Econ. Envir. Implic. Banff, AB, Canada, Jul. 1999, 84-94.
Long, R.B. et al., 1989, Studies in Petroleum Composition § Revue de ● Institute Francais du Petrole, abstract.
Long, R.B., 1979, The Concept of Asphaltenes§ Preprints, Div. Petroleum Chemistry, American Chemical Society, 24, 891-901.
Magaril, R.Z. et al., 1968, Study of the Mechanism of Coke Formation in the Cracking of Petroleum Resins, International Chemical Engineering 8 (4), 727.

McClements, D.J., Ultrasonic Measurements in Particle Size Analysi▲, University of Massachusetts, Amherst, USA, Encyclopedia of Analytical Chemistry (Applications, Theory and Instrumentation) pp. 5581-5587.
Pal R. et al., 1989, Viscosity/Concentration Relationships for Emulsions. Journal of Rheology, 33 (7), 1021-1045.
Pauli, A.T. 1996, Asphalt Compatibility Testing Using the Automated Heithaus Titration Test§ Preprints, Division of Fuel Chemistry, American Chemical Society, 41 (4), 1276-1281.
Pauli, A.T. et al., 1998, Relationships Between Asphaltenes, Heithaus Compatibility Parameters, and Asphalt Viscosity. Petrol. Science and Technology, 16 (9&10), 1125-1147.
Pauli, A.T. et al., Stability and Compatibility Testing of Petroleum and Asphalt§ American Laboratory, Sep. 2003, 2 pages.
Phillips, C.R, et al. 1985, Kinetic Models for the Thermal Cracking of Athabaska Bitumen, Fuel 64(5), 678-691.
Scatchard, G. 1931, Equilibria in Non-Electrolyte Solutions in Relation to the Vapor Pressure and Densities of the Components§ Chemical Reviews, 321-333.
Schabron, J.F. et al. Coking indexes using the Heithaus titration and asphaltene solubiliti , Preprints American Chemical Society, Division of Petroleum Chemistry (1999), 44(2), 187-189.
Schabron, J.F. et al., 1998, The Solubility and Three-Dimensional Structure of Asphaltenes§ Petroleum Science and Technology, 16 (3-4), 361-376.
Schabron, J.F. et al., 1999 Petroleum Residua Solubility Parameter/ Polarity Map: Stability Studies of Residua Pyrolysis§ Department of Energy Report under contract # DE-FC26-98FT40322 Task, 1.2, 24 pages.
Schabron, J.F. et al., 2000 Deposition from Heavy Oils § Department of Energy Report under contract # DE-FC26-98FT40322, 35 pages.
Schabron, J.F. et al., 2001b, Molecular Weight / Polarity Map for Residua Pyrolysis, Fuel, 80 (4), 529-537.
Schabron, J.F. et al., 2001c, Non-Pyrolytic Heat Induced Deposition from Heavy Oils, Fuel, 80 (7) 919-928.
Schabron, J.F., et al., 2002b, Residua Coke Formation Predictability Maps, Fuel, 81 (17) 2227-2240.
Schabron, J.F. et al., 2001a, Predicting Coke Formation Tendencies, Fuel, 80 (10) 1435-1446.
Schabron, J.F. et al., 2002a, Characterization of Residua During Pyrolysis, Preprints, Div. of Petroleum Chemistry, American Chemical Society, 47 (1), 17-21.
Schabron, J.F. et al., 1993, The Characterization of Petroleum Residua§ U.S. Dept of Energy Report under contract # DE-FC21-86MC11076I, 68 pages.
Schabron, J.F. et al., 2002, Thermal Analysis for Monitoring Incipient Coke Formatio■, US Department of Energy Report DE/FG36/01G011018, 18 pages.
Schabron, J.F. et al, 2002, Coke Formation Process Model for Petroleum Refining Efficiency Improvemen▼, US Department of Energy Report under contract # DE/FG36/01G011018, 40 pages.
Schabron, J.F. et al., 2004, Refinery Efficiency Improvement Ultrasonic Spectroscopy and WRI Coking Indexes, WRI Report 04-R009 to DOE under Cooperative Agreement DE-FC26-98FT40322.
Singh, I.D., V. Kothiyal, V. Ramaswamy, and R. Krishna, 1990, Characteristic Changes of Asphaltenes During Visbreaking of North Gujarat Short Residue. Fuel, 69 (3), 28+ 292.
Small, P.A., 1953, Some Factors Affecting the Solubility of Polymers§ Journal of Applied Chemistry, 71-80.
Snyder, L.R., 1968, Principles of Adsorption Chromatography§ Marcel Dekker, Inc., New York, 206-210.
U.S. Appl. No. 60/711,599, filed Aug. 25, 2005, entitled Rapid Determination of Asphaltenes and the Cyclohexane Soluble Portion of Asphaltenes by Automated On-Column Precipitation and Re-Dissolution; Specification 24 pages, Drawings 8 pages.
Wiehe, I.A., 1993, A Phase-Separation Kinetic Model for Coke Formation, Ind. Eng. Chem. Res., 32 (11), 244✕ 2454.

(56) References Cited

OTHER PUBLICATIONS

Wiehe, I.A., 1996, Two-Dimensional Solubility Parameter Mapping of Heavy Oils Fuel Science and Technology International, 14 (1&2), 289-312.
Bodusynski, M.S. et al., 1987, "Composition of heavy petroleums: 1. molecular weight, hydrogen deficiency, and heteroatom concentration as a function of atmospheric equivalent boiling point up to 1400 degrees F" Energy & Fuels, 1, 2-11.
Schabron, J.F., et al., 2006, "Initial studies using ultrasonic spectroscopy for monitoring changes in residua with pyrolysis," Fuel 85, 2093-2105.
Chiantore, Oscar and Simonelli, Alessandra, "Precipitation-redissolution Liquid Chromatography of Styrene-ethyl Acrylate Copolymers," Polymer Engineering and Science, Aug. 1999, vol. 39 No. 8, p. 1383-1388.
Cortell, Jessica M. et al., "Infulence of Vine Vigor on Grape (Vitis vinifera L. Cv. Pino Noir) Anthrocyanins. 2. Anthocyanins and Pigmented Polymers in Wine," J. Agric. Food Chem. 2007, 55, p. 6585-6595.
Aske, Narve et al.; "Determination of Saturate, Aromatic, Resin, and Asphaltenic (SARA) Components in Crude Oils by Means of Infrared and Near-Infrared Spectroscopy," Energy & Fuels, 2001, 15, 1304-1312.
Corbett, L.W., "Composition of Asphalt Based on Generic Fractionation, Using Solvent Deasphaltening, Elution-Adsorption Chromatography, and Densimetric Characterization," Analytical Chemistry, p. 576.
McCarthy, James E. et al.; "EPA's Regulation of Coal-Fired Power: Is a "Train Wreck" Coming?", Congressional Research Service, CRS Report for Congress, Aug. 8, 2011, 7-5700, R41914.
"Standard Test Method for n-Heptane Insulbles1", Designation: D 3279-97 (Reapproved 2001).
Spectra Analysis, Fully-Automated HPLC-FTIR Detection System, https://www.laboratoryequipment.com/news/2010/10/fully-automated-hplc-ftir-detection-system, Oct. 19, 2010.
Wilt et al., Determination of Asphaltenes in Petroleum Crude Oils by Fourier Transform Infrared Spectroscopy, Marathon-Ashland Petroleum L.L.C., Kentucky.
Aske et al., Determination of Saturate, Aromatic, Resin, and Asphaltenic (SARA) Components in Crude Oils by Means of Infrared and Near-Infrared Spectroscopy, The Norwegian University of Science and Technology, Trondheim, Norway Jun. 29, 2001.
Melendez et al., Prediction of the SARA analysis of Colombian crude oils using ATR-FTIR spectroscopy and chemometric methods, Elsevier B.V., Columbia, 2012.
Andersen, Separation of Asphalteness by Polarity Using Liquid-Liquid Extraction, Petroleum Science and Technology, Lyngby, Denmark, 1997.
Riveros et al., Determination of Asphaltene and Resin Content in Venezuelan Crude Oils by Using Fluorescence Spectroscopy and Partial Least Squares Regression, Energy & Fuels, Venezuela, 2006.
Al-Muhareb et al., Characterization of Petroleum Asphaltenes by Size Exclusion Chromatography, UV-fluorescence and Mass Spectrometry, Petroleum Science and Technology, London, UK, 2007.
Lehrer et al., Gel Permeation Chromatography of Asphalts and Asphaltenes, Die Makromolekulare Chemie, 1965.
Leontaritis et al., Fast Crude-Oil Heavy-Component Characterization Using Combination of ASTM, HPLC, and GPC Methods, Journal of Petroleum Science and Engineering, Netherlands, 1989.
Acevedo et al., Molecular weight properties of asphaltenes calculated from GPC data for octylated asphaltenes, Elsevier Science, LTD, Great Britian, 1998.
Trejo et al., Characterization of Asphaltenes from Hydrotreated Products by SEC, LDMS, MALDI, NMR, and XRD, American Chemical Society, May 31, 2007.
Dong et al., Size-Exclusion Chromatography of Asphaltenes: An Experimental Comparison of Commonly Used Approaches, Springer-Verlag, 2013.
Akmaz et al., The Structural Characterization of Saturate, Aromatic, Resin, and Asphaltene Fractions of Batiraman Crude Oil, Petroleum Science and Technology, Jan. 2011.
Leon et al., Determination of Molecular Weight of Vacuum Residue and their Sara Fractions, Ciencia, Tecnología y Futuro, Columbia, 2010.
Andersen, Concentration Effects in HPLC-SEC Analysis of Petroleum Asphaltenes Journal of Liquid Chromatography & Related Technologies, Denmark, Sep. 23, 2006.
Andersen et al., Asphaltene Precipitation and incipient Flocculation in Mixed Solvents, Danish Natural Science Research Council, Denmark.
Acevedo et al., Asphaltenes and resins from the basin, INTEVEP, S.A., Venezuela, Nov. 7, 1984.
Andersen, et al., Asphaltene Precipitation and Incipient Flocculation in Mixed Solvents, Danish Natural Science Research Council and Western Research Institute, Copenhage, Denmark, Laramie, WY.
Andersen, Concentration Effects in HPLC-SEC Analysis of Petroleum Asphaltenes, Journal of Liquid Chromatography & Related Technologies, Lyngby, Denmark, Sep. 23, 2006.
Acevedo et al., Asphaltenes and resins from the basin, Universidad Central de Venezuela, Facultad de Ciencias, Venezuela, Nov. 7, 1984.
Carr et al., Glossary of HPLC/LC Separation Terms, LCGC North America, North America, Feb. 1, 2008.
Altgelt et al., GPC Separation and Integrated Structural Analysis of Petroleum Heavy Ends, Separation Science, Richmond, CA, 1970.
Bishara, A New Approach for the Determination of MSD of Asphalt Cement Using HPGPC, Fuel Science & Technology International, Topeka, KS, 1992.
Branthaver, Binder Characterization and Evaluation vol. 2: Chemistry, Strategic Highway Research Program, National Research Council, Washington, DC, Nov. 1993.
Brule et al., Relationships Between Composition, Structure, and Properties of Road Asphalts: State of Research at the French Public Works Central Laboratory, Transportation Research Record.
Carbognani, Fast Monitoring of C20-C160 Crude Oil Alkanes by Size-Exclusion Chromatography-Evaporative Light Scattering Detection Performed with Silica Columns, Journal of Chromatography, Venezuela, 1997.
Dreessen et al., Durability Study: Field Aging of Conventional and Polymer Modified Binders, Total RM, Laboratory of traffic facilities, Switzerland, France, Jul. 31, 2009.
Haley, Changes in Chemical Composition of a Kuwait Short Residue during Air Blowing, School of Highway Engineering, University of New South Wales, Kensington, Australia, Dec. 1975.
Jennings et al., HP-GPC Analysis of Asphalt Fractions in the Study of Molecular Self-Assembly in Asphalt, Department of Chemistry and Biochemistry, Gaines Hall, Montana State University, Bozeman, MT.
Kim, et al., Use of GPC Chromatograms to Characterize Aged Asphalt Cements, J. Mater. Civ. Eng., 1993.
Le Guern et al., Physico-Chemical Analysis of Five Hard Bitumens: Identification of Chemical Species and Molecular Organization Before and After Artificial Aging, Elsevier Ltd., France, Apr. 29, 2010.
Lesueur, The Colloidal Structure of Bitumen: Consequences on the Rheology and on the Mechanisms of Bitumen Modification, Eurovia España, Pol. Ind. Villapark—Avda Quitapesares, Madrid, Spain, Sep. 9, 2008.
McCann et al., Instrumental Method Suitable for the Detection of Polymers in Asphalt Binders, U.S. Forest Service, Region 8—Engineering, Western Research Institute, Georgia, Wyoming, Jul. 20, 2007.
Pribanic et al., Use of a Multiwavelength UV-VIS Detector with HP-GPC to Give a Three-Dimensional View of Bituminous Materials, Transportation Research Record, France, Montana.
Redelius et al., Relation Between Bitumen Chemistry and Performance, Elsevier Ltd., 2014.
Schabron et al., Molecular Weight Polarity Map for Residua Pyrolysis, Elsevier Science Ltd., Laramie, WY, Jun. 9, 2000.
Wahhab et al., Prediction of Asphalt Rheological Properties Using HP-GPC, Journal of Materials in Civil engineering, Feb. 1999.

(56) References Cited

OTHER PUBLICATIONS

Vo-Dinh, Multicomponent Analysis by Synchronous Luminescence Spectrometry, Analytical Chemistry, Oak Ridge, Tennessee, Mar. 1978.
Zander et al., Regularities in the fluorescence spectra of coal-tar pitch fractionsCastrop-Rauxel, FRG, Miilheim a.d. Ruhr, FRG, May 16, 1990.
Kershaw, Fluorescence Spectroscopic Studies of Mesophase Formation, Fuel, Victoria, Australia, Oct. 18, 1994.
Groenzin et al., Asphaltene Molecular Size and Structure, J. Phys. Chem., Ridgefield, Connecticut, Jul. 27, 1999.
Groenzin et al., Molecular Size and Structure of Asphaltenes from Various Sources, Energy & Fuels, Ridgefield, Connecticut, Feb. 10, 2000.
Buenrostro-Gonzalez et al., The Overriding Chemical Principles that Define Asphaltenes, Energy & Fuels, Ridgefield, Connecticut, Apr. 10, 2001.
Ancheyta et al., Extraction and Characterization of Asphaltenes from Different Crude Oils and Solvents, Energy & Fuels, Mexico, Dec. 21, 2001.
Ryder, Quantitative Analysis of Crude Oils by Fluorescence Lifetime and Steady State Measurements using 380-nm Excitation, Society for Applied Spectroscopy, Galway, Ireland, 2002.
Groenzin, Molecular Size of Asphaltene Solubility Fractions, Energy & Fuels, University Park, Pennsylvania, Sep. 26, 2001.
Buch, Molecular Size of Asphaltene Fractions Obtained from Residuum Hydrotreatment, Elsevier Science Ltd., Lyngby, Denmark, Mexico, Dec. 12, 2002.
Riveros, Determination of Asphaltene and Resin Content in Venezuelan Crude Oils by Using Fluorescence Spectroscopy and Partial Least Squares Regression, Energy & Fuels, Caracas, Venezuela, Oct. 14, 2005.
Badre, Molecular Size and Weight of Asphaltene and Asphaltene Solubility Fractions from Coals, Crude Oils and Bitumen, Elsevier Science Ltd., Ridgefield, CT, Sendai, Japan, May 31, 2005.
Schneider et al., Asphaltene Molecular Size by Fluorescence Correlation Spectroscopy, Energy & Fuels, Cambridge, Massachusetts, Terre Haute, Indiana, Jun. 20, 2007.
E. Rogel et al., "Asphaltene Stability in Crude Oil and Petroleum Materials by Solubility Profile Analysis," Energy and Fuel, 24 (8), pp. 4369-4374 (2010) (Published on Web Jul. 28, 2010).
F.P. Burke et al., "Liquid Column Fractionation: A Method of Solvent Fractionation of Coal Liquefication and Petroleum Products," Fuel, vol. 58, pp. 539-541 (1979).
F.K. Schweighart et al., "Development of SRC-I Product Analysis. vol. 2. Evaluation of Analytical Techniques for SRC-I Characterization, Recycle Solvent Studies, and Product Fractionation Studies," published Sep. 1, 1983.
M.M. Boduszynski, "Composition of Heavy Petroleums. 1. Molecular Weight, Hydrogen Deficiency, and Heteroatom Concentration as a Function of Atmospheric Equivalent Boiling Point up to 1400 F (760 C)," Energy & Fuels, vol. 1, No. 1, pp. 2-11 (1987).
M.M. Boduszynski et al, "Separation of Solvent0Refined Coal into Solvent-Derived Fractions," Analyical Chemistry, vol. 54, pp. 372-375 (1982).
Parallel U.S. Appl. No. 13/243,782, Office action dated Jun. 27, 2012. 9 pages.
Parallel U.S. Appl. No. 13/243,782, Notice of Allowance dated Aug. 3, 2012. 9 pages.
Ovalles, C. et al. Predicting Reactivity of Feedstocks to Hydroprocessing by Using Asphaltene Characterization Techniques. Prepr. Pap.-Am. Chem. Soc., Div. Energy Fuels Chem. 2012, 57(2), 763. 3 pages.
Rogel, E. et al. Sediment Formation in Residue Hydroconversion Processes and Its Correlation to Asphaltene Behavior. Prepr. Pap.-Am. Chem. Soc., Div. Energy Fuels Chem. 2012, 57(2), 745.
Schabron, J.F. Use of the Asphaltene Determinator™ Method to Monitor Vacuum Residue Stability to Improve Refinery Distillation Efficiency, 2011.
Parallel U.S. Appl. No. 13/490,307; Office action dated Oct. 4, 2012. 10 pages.
McLean J. B. et al. Reactivity Screening of Feedstocks for Catgalytic Coal/Oil Co-Processing, Sep. 1986, http://web.anl.gov/PCS/acsfuel/preprint%20archive/Files/31_4_ANAHEIM_09-86_0169.pdf. 12 pages.
Mariaca-DomAnguez et al. "Reactivity of Fluid Catalytic Cracking Feedstocks as a Function of Reactive Hydrogen Content", Petroleum Science and Technology, 2004, vol. 22, Issue 1-2, pp. 13-29.
Johnson and Moyse, "Pretreatment of resid FCC feedstocks", Jul. 2004, http://www.digitalrefining.com/article/1000161.
Parallel U.S. Appl. No. 12/970,535, Notice of Allowance dated Jun. 8, 2012. 8 pages.
Baker, C. A. et al. A new chromatographic procedure and its application to high polymers, J. Chem. Soc., 1956, 2352-2362.
Parallel U.S. Appl. No. 13/600,039; Office action dated Nov. 19, 2012. 24 pages.
Parallel U.S. Appl. No. 13/490,316; Notice of Allowance dated Dec. 10, 2012.
Barman, B.N.; Crude Oil: Liquid Chromatography; 2000; Academic Press. 47 pages.
U.S. Appl. No. 13/237,568, filed Sep. 20, 2011. First Named Inventor: John F. Schabron.
Ovalles, C. et al. Characterization of Heavy Crude Oils, Their Fractions, and Hydrovisbroken Products by the Asphaltene Solubility Fraction Method, dx.doi.org/10.1021/ef201499f | Energy Fuels 2012, 26, 549-556, Published: Dec. 7, 2011.
Lopez-Linares, F. et al. Adsorption of Athabasca Vacuum Residues and Their Visbroken Products over Macroporous Solids: Influence of Their Molecular Characteristics, dx.doi.org/10.1021/ef201047z | Energy Fuels 2011, 25, 4049-4054, Published Aug. 17, 2011.
Rogel, E., Asphaltene Chemical Characterization as a Function of Solubility: Effects on Stability and Aggregation, dx.doi.org/10.1021/ef2013979 | Energy Fuels, Published Nov. 7, 2011.
Schabron, J. F. et al. The Waxphaltene Determinator Method for Automated Precipitation and Re-Dissolution of Wax and Asphaltene Components, Energy Fuels, Article ASAP, DOI: 10.1021/ef300184s, Feb. 27, 2012.
Parallel U.S. Appl. No. 12/970,535, Office action dated Mar. 2, 2011.
Parallel U.S. Appl. No. 12/970,535, Office action dated Oct. 7, 2011.
Parallel U.S. Appl. No. 12/970,535, Office action dated Jan. 12, 2012.
Parallel U.S. Appl. No. 13/243,782, Office action dated Mar. 23, 2012.
Parallel U.S. Appl. No. 12/970,535, Notice of Allowance dated Jun. 8, 2012.
Parallel U.S. Appl. No. 13/243,782, Office action dated Jun. 27, 2012.
Schabron, J. F. et al., Asphaltene Determinator Method for Automated On-Column Precipitation and Redissolution of Pericondensed Aromatic Asphaltene Components. Energy Fuels 2010, 24, 5984-5996.
Standard Test Method for Separation of Asphalt into Four Fractions. Designation: D4124-09. 383-390.
Steffens et al., Application of Fluorescence to the Study of Crude Petroleum, Springer Science+Business Media, LLC, Brazil, Dec. 14, 2009.
Cho et al., Application of Saturates, Aromatics, Resins, and Asphaltenes Crude Oil Fractionation for Detailed Chemical Characterization of Heavy Crude Oils by Fourier Transform Ion Cyclotron Resonance Mass Spectrometry Equipped with Atmospheric Pressure Photoionization, ACS Publications, Korea, 2012.
Abou-Hatab, Substituent Effects on the Absorption and Fluorescence Properties of Anthracene, The Journal of Physical Chemistry, Philadelphia, Pennsylvania, Princeton, New Jersey, Jan. 19, 2017.
Yarranton et al., Regular Solution Based Approach to Modeling Asphaltene Precipitation from Native and Reacted Oils: Part 2, Molecular Weight, Density, and Solubility Parameter of Saturates, Aromatics, and Resins, Elsevier Ltd., Canada, Netherlands, Nov. 19, 2017.
Hussein, Characterization of Petroleum Crude Oils using Laser Induced Fluorescence, Journal of Petroleum & Environmental Biotechnology, Cairo, Egypt, 2015.

(56) References Cited

OTHER PUBLICATIONS

Sylvia et al., Durability Study: Field Aging of conventional and Polymer Modified Binders, TRB 2010 Annual Meeting CD-ROM, France, Switzerland, Jul. 31, 2009.
McKay et al., Flourescence Spectroscopy in the Characterization of High-Boiling Petroleum Distillates, Laramie Energy Research Center, Bureau of Mines, U.S. Dept. of the Interior, Laramie, Wyoming.
McCann et al., Instrumental Method Suitable for the Detection of Polymers in Asphalt Binders, Transportation Research Board, Atlanta, Georgia, Laramie, Wyoming, Jul. 20, 2007.
Karpicz et al., Laser Flourosensor for Oil Spot Detection, Institute of Physics, Vilnius, Lithuania.
Ryder, Analysis of Crude Petroleum Oils Using Flourescence Spectroscopy, Department of Chemistry, and National Centre for Biomedical Engineering Science, National University of Ireland—Galway, Galway, Ireland.
Related U.S. Appl. No. 11/510,491, Notice of Allowance dated Nov. 17, 2010.
Related U.S. Appl. No. 13/490,316; Office action dated Aug. 3, 2012.
Agilent Technologies 1260 Infinity Variable Wavelength Detector Manual G1314-90013, Rev. C, Nov. 2013.
Agilent Technologies 1260 Infinity Diode Array and Multiple Wavelength Detector Manual G1315-90015 Rev. C, Jul. 2018.
Wavelength Standards for the Near-Infrared Spectral Region, Apr. 1, 2007, Spectroscopy,vol. 23, Issue 4.
The U.S.'s Most Commonly Recycled Material? Asphalt Pavements http://www.asphaltpavement.org/index.php?option=com_content &view=article&id=1146:the-u-s-s-most-commonly-recycled-material-asphalt-pavements&Itemid=767.
Effects of aging on the properties of asphalt, P.E.YuhongWang,, KechengZhao, CharlesGlover.
LingChen,YongWen, DanChong, ChichunHu, Construction and Building Materials, vol. 80, Apr. 2015.
Influence of six rejuvenators on the performance properties of Reclaimed Asphalt Pavement (RAP) binder and 100% recycled asphalt mixtures, Martins Zaumanis, Rajib Mallick,Lily Poulikakis, Rober Frank, Construction and Building Materials, vol. 71, Nov. 2014.
SHRP-A-645, SHRP Materials Reference Library: Asphalt Cements:A Concise Data Compilation David R. Jones, IV, Asphalt Research Program, The University of Texas at Austin.
The Use of Spectrophotometry UV-Vis for the Study of Porphyrins, Rita Giovannetti, University of Camerino, Chemistry Section of School of Environmental Sciences, Camerino, Italy.
Abou-Hatab, S., V. A. Spata, and S. Matsika. 2017. "Subsituent Effects on the Absorption and Fluorescnce Properties of Antrhacene." Journal of Phyical Chemistry A 1213-1222.
Al-hajji, A., and O. R. Koseoglu. 2016. Characterization of Crude Oil and Its Fractions by Fluorescence Spectroscopy Analysis. International Patent 2016/111956.
Al-Muhareb, E., T. J. Morgan, A. A. Herod, and R. Kandiyoti. 2007. "Characterization of Petroleum Asphaltenes by Size Exlusion Chromotography, UV-fluorescence and Mass Spectrometry." Petroleum Science and Technolgy 81-91.
Groenzin, H., O. C. Mullins, S. Eser, J. Mathews, M.-G. Yang, and D. Jones. 2003. "Molecular Size of Asphaltene Solubility Fracitons." Energy Fuels 498-503.
Karpicz, R., A. Dementjev, Z. Kuprionis, S. Pakalnis, R. Westphal, R. Reuter, and V. Gulbinas. 2005. "Laser Fluorosensor for Oil Spot Detection." Lithuanian Journal of Physics 213-218.
M. Zander, M. W. Haenel. 1990. "Regularities in the Fluoescence Spectra of Coal-tar Pitch Fractions." Fuel 1206-1207.
Mullins, O. C. 1999. "Optical Interrogation of Aromatic Moieties in Crude Oils and Asphaltenes." In Structures and Dynamics of Asphaltenes, by E. Y. Sheu O. C. Mullins, 21-77. New York: Plenum Press.
Scott R., and L. Montanari. 1998. "Molecular Structure and Intermolecular Interaction of Asphaltenes by FT-IR, NMR, EPR." In Structure and Dynamics of Asphaltenes, by O. C. Mullins and Eric Y. Sheu, 93-95. New York: Plenum Press.
Petersen J.C., Quantitative Functional Group Analysis of Asphalts Using Differential Infrared Spectrometry and Selective Chemical Reactions—Theory and Application, Transportation Research Record, 1986;1096:1.
J. Lamontagne, P. Dumas, V. Mouillet, J. Kister, Comparison by Fourier transform infrared (FTIR) spectroscopy of different ageing techniques: application to road bitumens, Fuel 80 (2001) 483-488.
V. Mouillet, J. Lamontagne, F. Durrieu, J-P. Planche, L. Lapalu, "Infrared microscopy investigation of oxidation and phase evolution in bitumen modified with polymers", Fuel 87 (2008) 1270-1280.
Recycling of polyethylene terephthalate (PET) plastic bottle wastes in bituminous asphaltic concrete Adebayo Olatunbosun Sojobi1*, Stephen Emeka Nwobodo1 and Oluwasegun James Aladegboye1, Cogent Engineering (2016), 3: 1133480.
Brûlé B, Migliori F., 1983, Application de la chromatographie sur gel perméable à la caractérisation de bitumes routiers et de leur susceptibilité au vieillissement artificiel. Bulletin de Liaison Laboratoire des Ponts Chaussées; 128:107-20.
Haley, G. A., 1975, Changes in chemical composition of Kuwait short residue during air blowing. Analytical Chemistry, 47 (14): 2432-2437.
"Energy and Environmental Profile of the US Petroleum Refining Industry," 1988, Prepared by Energetics Inc. for U.S. Department of Energy Office of Industrial Technologies. 124 pages.
Burrell, H., 1955, Solubility Parameters. Interchemical Review, 3-16, 32-46.
Cartz, L., ch. 3, Ultrasonic Testing, Nondestructive Testing, 1995, pp. 81-98.
Del Bianco, A. et al., 1993, Thermal Cracking of Petroleum Residues 1. Kinetic Analysis of the Reaction. Fuel, 72 (1). 81-85.
Heithaus, J.J., 1962, Measurement and Significance of Asphaltene Peptization. Journal of the Institute of Petroleum 48 (458), 45-53.
Hildebrand, J.H. et al., 1970, Regular and Related Solutions. Van Nostrand Reinhold, NY, pp. 24-27, pp. 152-153, pp. 212-215.
Jones et al. Development of an ultrasonic oil stability monitor for the assessment of asphaltene aggregation in hydrocarbon streams, Proceed. Intern. Conf. Mitigat. Heat Exch. Foul. Econ. Envir. Implic. Banff, AB, Canada, Jul. 1999, 84-94.
Long, R.B. et al., 1989, Studies in Petroleum Composition. Revue de Institute Francais du Petrole, abstract.
Long, R.B., 1979, Chemistry of Asphaltenes. Preprints, Div. Petroleum Chemistry, American Chemical Society, 24, 891-901.
McClements, D.J., Ultrasonic Measurements in Particle Size Analysis, University of Massachusetts, Amherst, USA, Encyclopedia of Analytical Chemistry (Applications, Theory and Instrumentation) pp. 1-8.
Pauli, A.T. 1996, Asphalt Compatibility Testing Using the Automated Heithaus Titration Test. Preprints, Division of Fuel Chemistry, American Chemical Society, 41 (4), 1276-1281.
Pauli, A.T. et al., Stability and Compatibility Testing of Petroleum and Asphalt. American Laboratory, Sep. 2003, 2 pages.
Scatchard, G. 1931, Equilibria in Non-Electrolyte Solutions in Relation to the Vapor Pressure and Densities of the Components. Chemical Reviews, 321-333.
Schabron, J.F. et al., 1998, The Solubility and Three-Dimensional Structure of Asphaltenes. Petroleum Science and Technology, 16 (3-4), 361-376.
Schabron, J.F. et al., 1999 Petroleum Residua Solubility Polarity Map: Stability Studies of Residua Pyrolysis. Department of Energy Report under contract # DE-FC26-98FT40322 Task, 1.2, 24 pages.
Schabron, J.F. et al., 2000 Deposition from Heavy Oils. Department of Energy Report under contract # DE-FC26-98FT40322, 35 pages.
Schabron, J.F. et al., 2002, Characterization of Residua During Pyrolysis, Preprints, Div. of Petroleum Chemistry, American Chemical Society, 47 (1), 17-21.
Schabron, J.F. et al., 1993, The Characterization of Petroleum Residua. U.S. Dept of Energy Report under contract # DE-FC21-86MC11076I, 68 pages.

(56) References Cited

OTHER PUBLICATIONS

Schabron, J.F. et al., 2004, Refinery Efficiency Improvement Ultrasonic Spectroscopy and WRI Coking Indexes, WRI Report 04-R009 to DOE under Cooperative Agreement DE-FC26-98FT40322. 46 pages.
Singh, I.D., V. Kothiyal, V. Ramaswamy, and R. Krishna, 1990, Characteristic Changes of Asphaltenes During Visbreaking of North Gujarat Short Residue. Fuel, 69 (3), 289-292.
Small, P.A., 1953, Some Factors Affecting the Solubility of Polymers Journal of Applied Chemistry, 71-80.
Snyder, L.R., 1968, Principles of Adsorption Chromatography. Marcel Dekker, Inc., New York, 206-210.
U.S. Appl. No. 60/711,599, filed Aug. 25, 2005.
Wiehe, I.A., 1993, A Phase-Separation Kinetic Model for Coke Formation, Ind. Eng. Chem. Res., 32 (11), 244x 2454.
Wiehe, I.A., 1996, Two-Dimensional Solubility Parameter Mapping of Heavy Oils Fuel Science and Technology International, 14 (1&2), 289-312.
Corbett, L.W., "Composition of Asphalt Based on Generic Fractionation, Using Solvent Deasphaltening, Elution-Adsorption Chromatography, and Densimetric Characterization," Analytical Chemistry, p. 576-579.
McCarthy, James E. et al.; "EPA's Regulation of Coal-Fired Power: Is a "Train Wreck" Coming?", Congressional Research Service, CRS Report for Congress, Aug. 8, 2011, 7-5700, R41914. 50 pages.
Parallel U.S. Appl. No. 13/243,782, Notice of Allowance dated Aug. 3, 2012.
Ovalles, C. et al. Predicting Reactivity of Feedstocks to Hydroprocessing by Using Asphaltene Characterization Techniques. Prepr. Pap.-Am. Chem. Soc., Div. Energy Fuels Chem. 2012, 57(2), 763.
Parallel U.S. Appl. No. 13/490,307; Office action dated Oct. 4, 2012.
McLean J. B. et al. Reactivity Screening of Feedstocks for Catgalytic Coal/Oil Co-Processing, Sep. 1986, http://web.anl.gov/PCS/acsfuel/preprint%20archive/Files/31_4_ANAHEIM_09-86_0169.pdf.
Parallel U.S. Appl. No. 13/600,039; Office action dated Nov. 19, 2012.
Barman, B.N.; Crude Oil: Liquid Chromatography; 2000; Academic Press.

\* cited by examiner

US 10,449,502 B2

METHODS FOR ANALYZING HYDROCARBONS AND HYDROCARBON BLENDS FOR CHEMICAL COMPOSITIONS

This application claims priority to U.S. Provisional App. No. 62/582,808 filed Nov. 7, 2017, and is a continuation-in-part application of U.S. patent application Ser. No. 15/358,991, filed Nov. 22, 2016, and is a continuation, and claims benefit of and priority to U.S. patent application Ser. No. 13/723,058, filed Dec. 20, 2012, which claims benefit of and priority to U.S. Provisional Application Ser. No. 61/700,090, filed Sep. 12, 2012, and said patent application Ser. No. 13/723,058 is a continuation-in-part of and claims benefit of and priority to, International Application number PCT/US2012/021317, filed Jan. 13, 2012 (published as publication number WO2012121804A1 on Sep. 13, 2012), which itself claims priority to and benefit of U.S. provisional patent application Ser. No. 61/450,515, filed Mar. 8, 2011, and U.S. patent application Ser. No. 13/723,058 is a continuation-in-part of, and claims benefit of and priority to, U.S. nonprovisional application Ser. No. 13/237,568, filed Sep. 20, 2011, and U.S. patent application Ser. No. 13/723,058 is a continuation-in-part application of, and claims benefit of and priority to U.S. nonprovisional application Ser. No. 13/600,039, filed Aug. 30, 2012, now issued as U.S. Pat. No. 8,492,154, which itself is a continuation of, and claims benefit of and priority to U.S. patent application Ser. No. 13/490,307, filed Jun. 6, 2012, now issued as U.S. Pat. No. 8,530,240, and U.S. patent application Ser. No. 13/490,316, filed Jun. 6, 2012, now issued as U.S. Pat. No. 8,367,425, each of which is a continuation of, and claims benefit of and priority to, U.S. nonprovisional application Ser. No. 13/243,782, filed on Sep. 23, 2011 (published as publication number US 20120016168 on Jan. 19, 2012), now issued as U.S. Pat. No. 8,273,581, which is itself a continuation application of, and claims benefit of and priority to, U.S. patent application Ser. No. 12/970,535, filed on Dec. 16, 2010 (published as publication number US 20110120950 A1 on May 26, 2011), now issued as U.S. Pat. No. 8,241,920, which itself is a continuation application of, and claims benefit of and priority to, U.S. patent application Ser. No. 11/510,491, filed Aug. 25, 2006 (published as publication number US 2007/0048874 A1 on Mar. 1, 2007), now issued as U.S. Pat. No. 7,875,464 (issued on Jan. 25, 2011) which itself is a United States non-provisional patent application and claims benefit of and priority to U.S. provisional patent application Ser. No. 60/711,599, filed Aug. 25, 2005, each said application and patent hereby incorporated herein by reference in its entirety.

GOVERNMENT LICENSE RIGHTS

This application relates to work performed under US DOE Cooperative Agreement DE-FC26-98FT40322. The US government may have certain rights in this inventive technology, including "march-in" rights, as provided for by the terms of US DOE Cooperative Agreement DE-FC26-98FT40322.

BACKGROUND OF THE INVENTION

Knowing the chemical composition of hydrocarbons (including but not limited to petroleum oils and asphaltic materials) is critical in diverse applications such as improving the performance of bituminous roadways as well as improving refining and oil production efficiency. Certain embodiments of the inventive technology disclosed herein combine innovative features that provide a. novel analysis of at least the maltene portion of hydrocarbons in an new manner. The data generated through use of the size exclusion chromatography (SEC) column (and the detector configured to measure at least one response for the SEC column eluate) provides valuable insight into compositional differences between different oils and asphalt binders, and various additives, polymers or modifiers the internal chemical changes which occur due to aging or processing, modification, blending, and processing generally. The results can be used in establishing compatibility, blending, formulating, controlling catalyst and/or additive or modifier use, modifying and for predictive modeling, process control, product quality control, and improving processing efficiency and yield, inter alia.

This inventive technology, in embodiments, involves a novel combination of two modes of separation/analysis for hydrocarbons such as, e.g., bitumen and oils, including but not limited to petroleum oils, asphalt, coal liquids and shale oils. In embodiments able to quantify asphaltenic constituents, one component of the combined separation is an automated solubility separation in which asphaltenes are precipitated within a ground polytetrafluoroethylene (PTFE)-packed column. This may be referred to as the Asphaltene Determinator (AD) separation, and may be as described in U.S. Pat. No. 7,875,464 (perhaps supplemented by disclosure herein), incorporated herein in its entirety. The SEC technology disclosed herein can have added to it steps/equipment that, like that SEC technology, may be directed towards analysis of the various maltene components, but using additional separation, adsorption equipment such as that disclosed in U.S. Pat. No. 9,353,317, incorporated herein in its entirety.

The present inventive technology, in particular embodiments, includes a variety of aspects which may be selected in different combinations based upon the particular application or needs to be addressed. In one basic form, the inventive technology relates to in-vessel retention of a material (e.g., asphaltenes on a stationary phase that is substantially chemically inert relative to such asphaltenes) that are removed (e.g., via precipitation) from a hydrocarbon that is entrained in and part of a solvent (e.g., precipitant) mobile phase (producing a first eluate), and perhaps later dissolution of that material (e.g., via a successive dissolution procedure) to produce at least one asphaltenic eluate, in addition to detectors and associated componentry. Such detectors and associated componentry may include a size exclusion chromatography stationary phase (e.g., in a column) and a detector coupled to the eluate therefrom, to analyze, e.g., maltenes of the hydrocarbon (in addition to detector(s) coupled to the asphaltenic eluate(s) from the inert column)), all as part of a processing and/or analysis operation. Advantages of the inventive technology relate to improvements in speed, efficiency, and accuracy, inter alia, relative to known material processing and analysis methods.

0 min. Heptane, 15 min. Cyclohexane, 30 min, Toluene, 40 min. Methylene Chloride, 50 min. Heptane, 4.0 mL/min.

Figure 3:
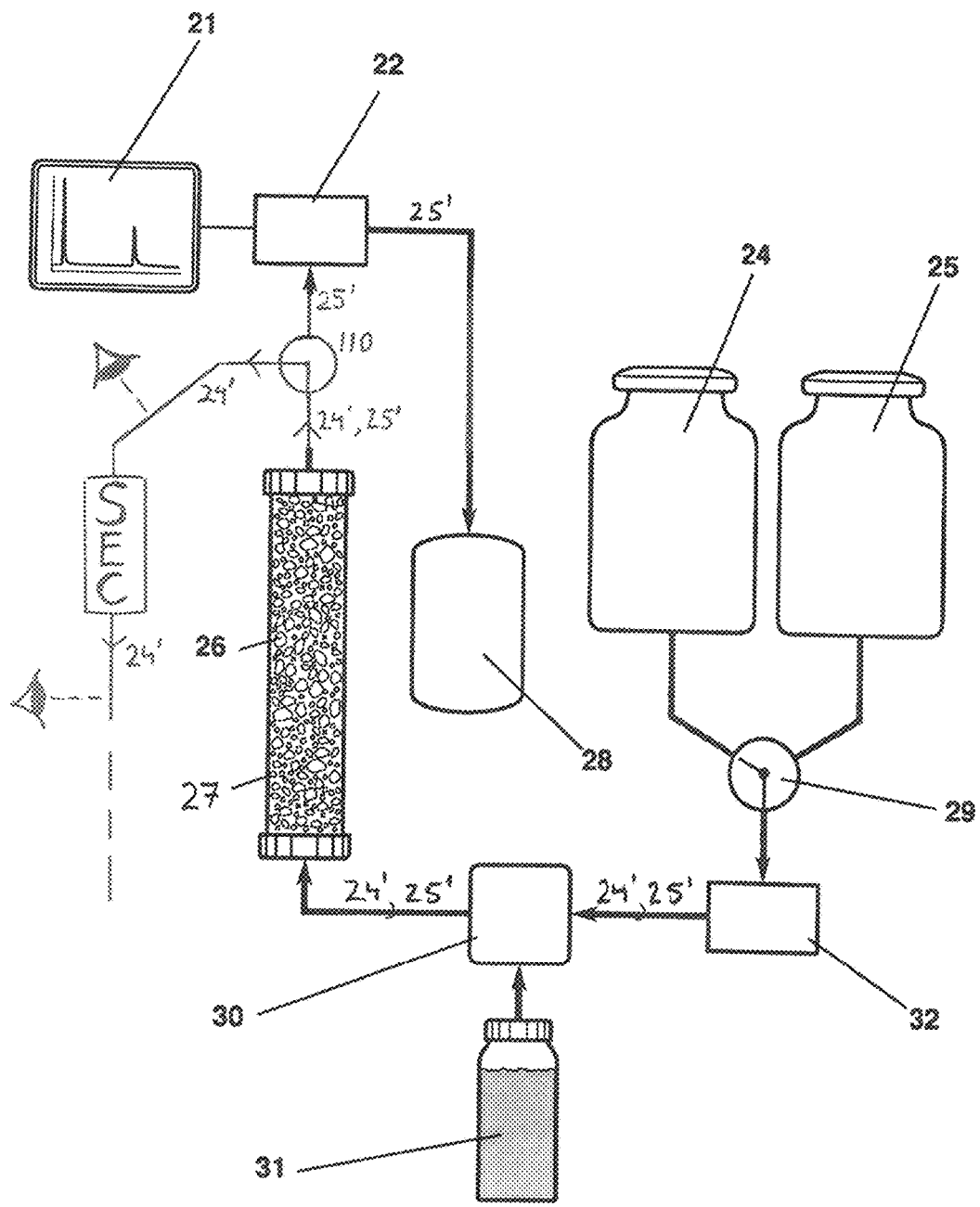

FIG. 3 shows a schematic of components of an apparatus, including a SEC column and a detector coupled to eluate therefrom, that may be used in certain embodiments of the inventive technology.

Figure 4:
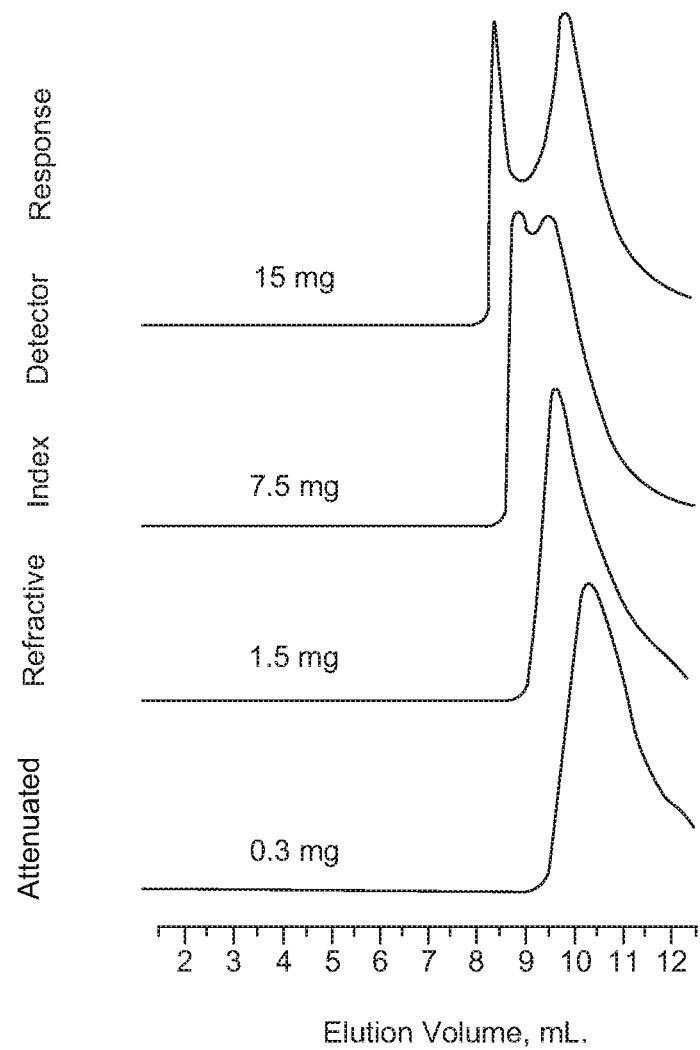

FIG. 4 shows a graph representing how association effects of a sample of asphaltenes affects the ability of a conventional SEC separation to determine an accurate molecular weight measurement.

Figure 5:
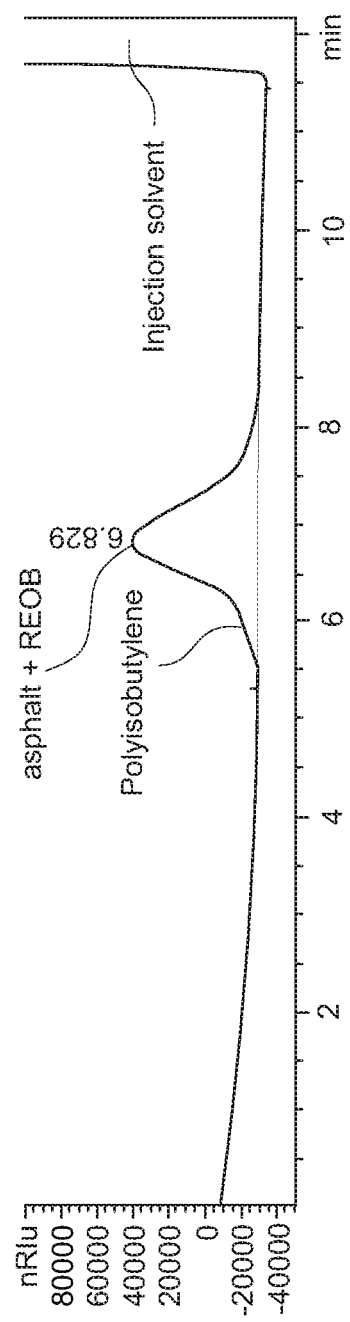

FIG. 5 shows a graph representing an AD+SEC separation of a deasphaltened asphalt sample that contains REOB.

Figure 6:
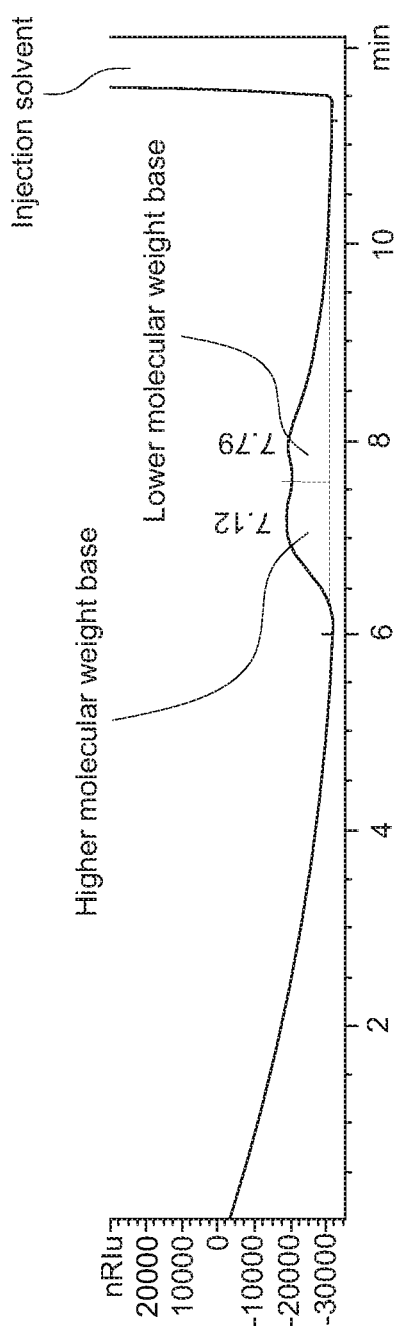

FIG. 6 shows a graph representing an AD+SEC separation of a deasphaltened asphalt sample that is a blend of two different asphalt sources.

Figure 7:
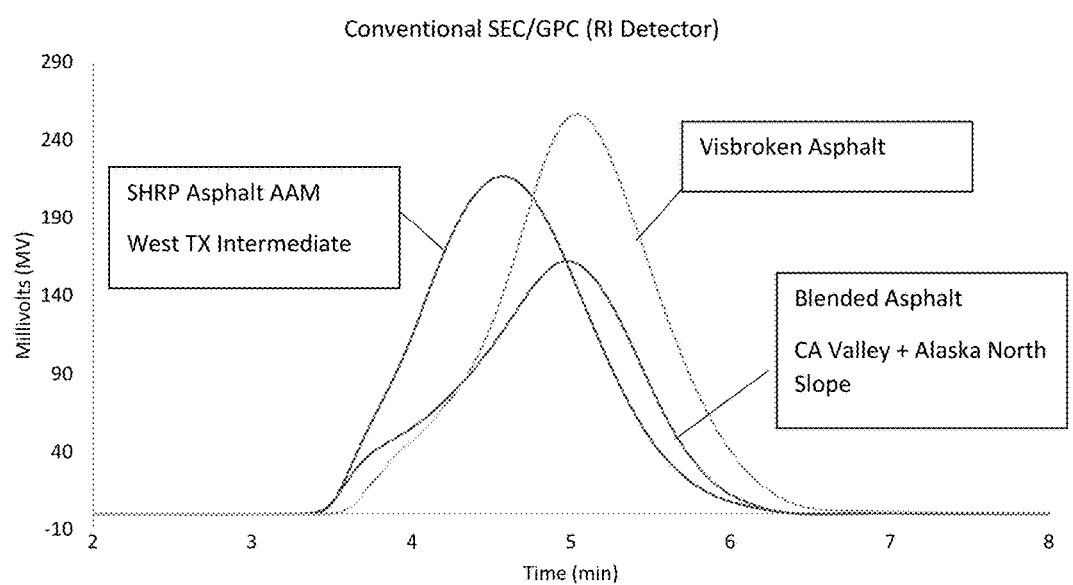

FIG. 7 shows a graph representing conventional SEC/GPC (RI Detector), including SHRP Asphalt AAM (West TX Intermediate), a Visbroken Asphalt, and a Blended Asphalt (CA Valley+Alaska North Slope).

Figure 8:
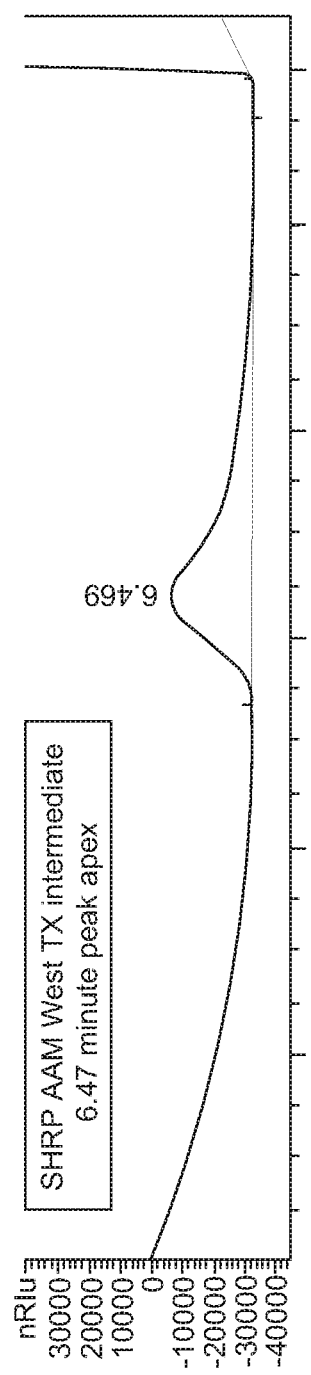

FIG. 8 shows a graph representing AD+SEC (deasphaltened) SHRP AAM West TX Intermediate with a 6.47 minute peak apex.

Figure 9:
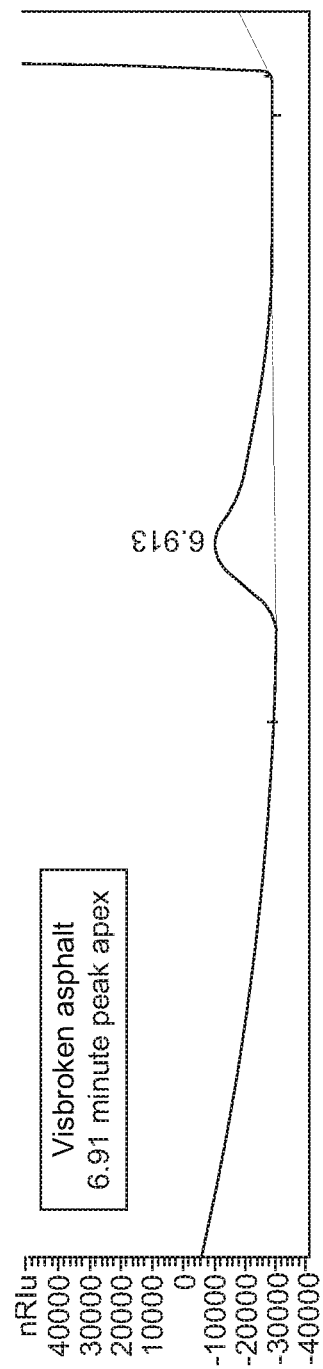

FIG. 9 shows a graph representing AD+SEC (deasphaltened) Visbroken Asphalt with a 6.91 minute peak apex.

Figure 10:
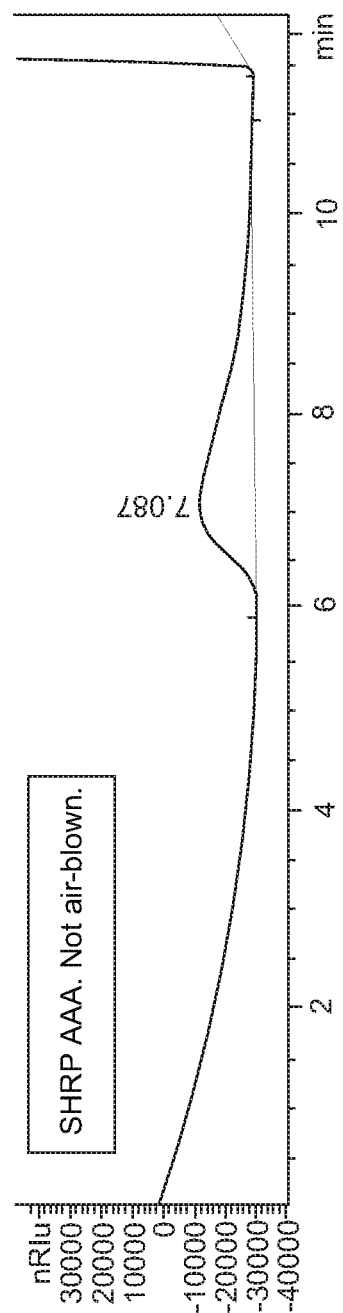

FIG. 10 shows a graph representing AD+SEC (deasphaltened) SHRP AAA, not air-blown.

Figure 11:
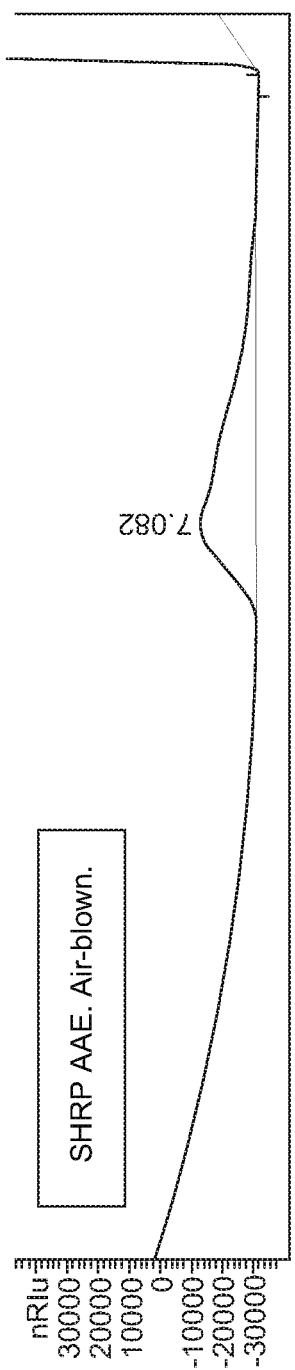

FIG. 11 shows a graph representing AD+SEC (deasphaltened) SHRP AAE, air blown.

Figure 12:
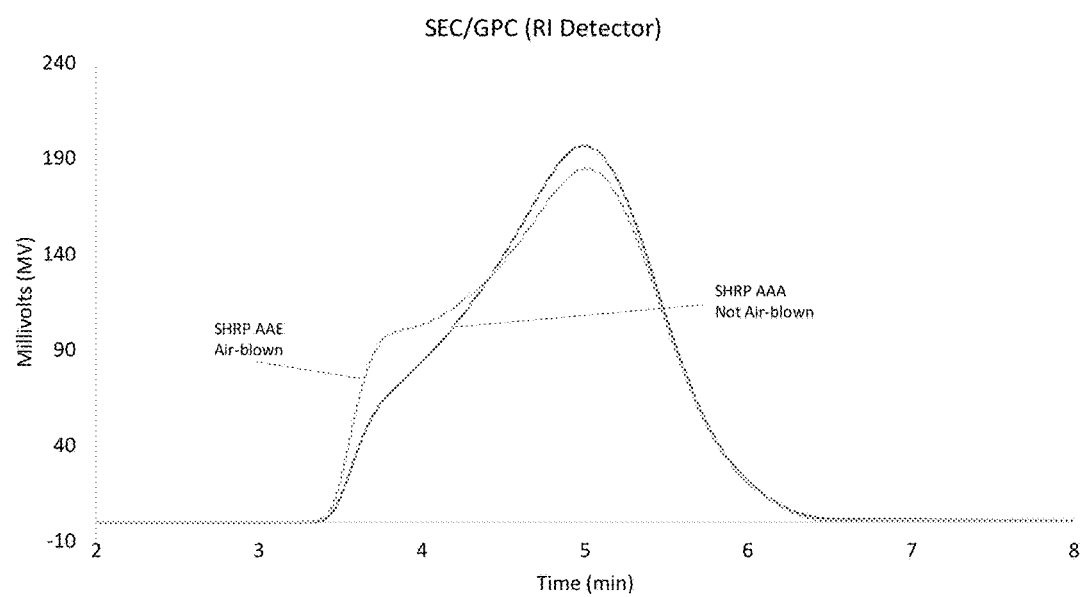

FIG. 12 shows a graph representing conventional SEC/GPC (RI Detector) for SHRP AAA (not air blown and AAE (air blown).

SUMMARY OF THE INVENTION

U.S. Pat. No. 7,875,464, incorporated herein in its entirety, may act as a basis of sorts for embodiments of this inventive technology. Inventive improvements disclosed in this application include additional chromatographic techniques and detection capabilities such as those involving SEC, to greatly increase the amount of meaningful chemical information that can be obtained.

The new techniques and capabilities provide more powerful methods to analyze extremely complex hydrocarbon blends.

The results of the detection can be subsequently analyzed using any chemometrics and/or deconvolution software and including but not limited to, those based on neural networks, partial least squares, principal component analysis or the ExpliFit multi linear regression software from WRI which is especially useful for applications where insufficient observations are available compared to the number of independent measurement variables available. These chemometric software can be used for the identification and quantification of the molecule families and for the determination of mathematical relationships between analytical these chemical measurements themselves coming from this technology, and further between chemical measurements and physical measurements.

Embodiments of the present invention may identify instrumental analyses that could measure the amount of asphaltenes in fossil fuel materials or correlate with coking indexes and perhaps lead to the development of a rapid analysis system.

It is therefore an object of certain embodiments of the present inventive technology to provide a rapid on-column precipitation and dissolution method for rapid measurement of a cyclohexane soluble portion of asphaltenes precipitated from a hydrocarbonaceous solution of interest.

It is an object of certain embodiments of the present inventive technology to provide an automated system for rapid measurement of a cyclohexane soluble portion of asphaltenes.

It is an object of certain embodiments of the present inventive technology to provide an in-vessel precipitation/dissolution system for improved processing (including but not limited to fractionating) of a solution of interest.

It is an object of certain embodiments of the present inventive technology to provide an in-vessel precipitation/dissolution system for improved analysis of a solution of interest (including but not limited to determining the solution's makeup relative to dissolved materials of different polarity).

It is an object of certain embodiments of the present inventive technology to provide an automated analysis and/or processing method using in-vessel material generation.

It is an embodiment of certain embodiments of the present inventive technology to provide an automated analysis to provide weight, molecular weight, size and/or volume-type information about components of maltenes of a hydrocarbon, in addition perhaps to providing information regarding asphaltene fractions, through the use of intentionally placed SEC stationary phases and detector(s).

Naturally, further objects, goals and embodiments of the inventions are disclosed throughout other areas of the specification.

DESCRIPTION OF VARIOUS EMBODIMENTS OF THE INVENTIVE TECHNOLOGY

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments are not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

At least one embodiment of the inventive technology may be a method that involves the use of size exclusion chromatography (SEC)-based analysis of maltenes eluting from a column, e.g., a column that houses a stationary phase that is substantially inert (relative to asphaltenes). Equipment that achieves such analysis (e.g., a SEC column, perhaps housing a gel permeation chromatography stationary phase) may be provided as an adjunct of sorts to equipment of the Asphaltene Determinator system of U.S. Pat. No. 7,875,464. Such patent discloses methods that, in particular embodiments, comprise the steps of establishing a precipitant in a vessel (a column 27 or a batch type vat 46, as but two examples) having a stationary phase (lattice type or packing material 26 that is substantially inert relative to asphaltenes, as but two examples) established therein; adding a hydrocarbon 31 (e.g., oil, or any other material, e.g., solution of interest, which one desires to process or analyze in any fashion) to the vessel; precipitating a material (e.g., a solid material, a viscous liquid material, and/or a gel material) from the hydrocarbon; and generating a first eluate (e.g., an asphaltene-free eluate, or a "maltenic" eluate) upon performing the step of precipitating a material from the hydrocarbon. The step of establishing a precipitant (any material that effects precipitation) in a vessel may be performed by adding the precipitant (heptane, pentane, and/or isooctane, as but a few examples) to the vessel in liquid form, but indeed other methods (e.g., adding a powder form of the precipitant to the vessel and then adding a dissolving liquid) may be used. It is of note that any vessel used for large scale processing (as opposed to analysis of a small sample such as an aliquot), is referred to as a batch type vessel.

The inert stationary phase may be in a column or batch type vat (as but two examples). Typically, but not necessarily, a column would be used when the method were employed for hydrocarbon analysis (measuring asphaltene content of an oil, determining the makeup of maltenes, or estimating an onset of coking that might occur during processing of oil, as but two of many examples), and the batch type vat would be used when processing a solution (fractionating oil, as but one of many examples). The stationary phase (whether lattice, packing material, or other) may be substantially inert in that, e.g., it is designed such that there is no or minimal interaction, such as adsorbance, of the stationary phase with the contacting solution or solute, in some embodiments. Substantially inert may include causing reactions that impair results—whether analytical or processing—to an acceptable degree. Glass bead packing material, for example, is not considered a substantially inert stationary phase. Such a substantially inert stationary phase includes but is not limited to oligomers or polymers of polytetrafluorethylene, also known as PTFE (Teflon), polyphenylene sulfide, silicon polymer, fluorinated polymers or elastomers (e.g., Vitons), or PEEK (polyether ether ketone) stationary phase. It is also of note that any of such stationary phases, whether packing material or lattice, or other, need not be solid (e.g., need not be solid PTFE, e.g.), but instead can indeed be only coated with the indicated material. Packing material can be beaded, ground, chipped, small rods, pebbled, or blocked, as but a few examples—essentially of any form that can be packed in a column.

One fact pointing to the non-obviousness of certain embodiments of the inventive technology is the precipitation of material on or within a substantially inert stationary phase, as columnar liquid chromatography requires adsorption effects (i.e., "non-inertness", or chemical interaction) between the stationary phase and passing substrates dissolved in solution for operation. It is also of note that for a stationary phase to be established in a vessel, it certainly need not, but may, fill most of or all of the entire volume of the vessel.

The precipitated asphaltenes may be in (not presented mutually exclusively) powdered form, granular form, layered form, coated form, and/or lump form, as but a few examples; it may be solid, gel, and/or viscous liquid. Often, what is seen is solid material that coats the stationary phase, or portions thereof (e.g., it may precipitate within the packing bed).

Typically, the precipitant solvent (e.g., of a first solvent mobile phase) will have a polarity that is sufficiently different from the solution of interest so as to effect precipitation of a material from the solution of interest. It is of note that the precipitant may also be referred to as a precipitant solvent in that there typically will be a remnant liquid (e.g., a remnant solution) as eluate from the inert stationary phase column, e.g., a first eluate, generated during the precipitation event; the term precipitant solvent may be appropriate in such instances because upon interaction of the precipitant with the hydrocarbon (a term that includes hydrocarbon dissolved in solvent, whether that solvent is added before the hydrocarbon is entrained (e.g., via injection) into a first mobile phase, and/or that solvent is the first mobile phase), some material (e.g., precipitant insoluble material) may be precipitated from the solution while other material (e.g., precipitant soluble material) may remain dissolved in what, after the precipitation, may be referred to as a first eluate (or maltenic eluate, or asphaltene-free (deasphaltened) eluate).

Examples of determining at least one characteristic include but are not limited to the following: determining a coking index, determining a solution constituent amount (e.g., determining an amount of heptane asphaltenes that are soluble in cyclohexane soluble or other solvents, determining a height or area of a peak of a separation profile, determining a fractional amount of precipitated material, determining a compositional makeup of maltenes, determining a compositional makeup of an asphalt, determining a polarity-based makeup of a solution). Such characteristics may be useful in control of one or more of the following: oil processing, oil fractionating, oil production processes, pipeline fouling, hydrotreating, distillation, vacuum distillation, atmospheric distillation, visbreaking, blending, asphalt formation, extraction, solvent deasphalteneing, catalytic cracking, mild or deep pyrolysis, coking onset estimation and fouling, as but a few examples. It is of note that an important application of embodiments of the inventive technology may be processes or analyses involving hydrocarbonaceous materials (hydrocarbons, e.g., asphalt and oil in any of its many forms, such as but not limited to crude oil, etc.). Further of note is the fact that the term solvent is a broad term that includes "pure solvents" (e.g., straight methylene chloride), in addition to solvent mixtures.

As mentioned, certain embodiments may focus on processing of the hydrocarbon (e.g., via batch processes, which may use, e.g., vat type vessels). Such processing may include, but is not limited to: fractionating the solution of interest (fractionating oil, as but one example), removing unwanted materials from the solution of interest, purification of the solution of interest, fractionation of an asphalt, extraction of a constituent of a hydrocarbon, and preparing the hydrocarbon for further processing.

Any analysis may be accomplished through the use of any of a number of detectors employing evaporative light scattering, mass spectrometry, conductivity, oxidation/reduction, refractive index, polarimetry, atomic spectroscopy, optical absorbance, x-ray, ultrasound, and/or fluorescence, as but a few of the available techniques. Such detection may occur as the analyzed substance leaves the vessel (e.g., column with inert stationary phase therein and/or column with SEC stationary phase therein), while it is in the vessel, or after it leaves the vessel. A typical setup of a detector may be not dissimilar to that found in some liquid chromatography set-ups, where the detector "detects" liquid (via measuring a response) as it elutes from the column (in the case of columnar, analytical embodiments), or as it is drained from a batch type vat (e.g., as in processing embodiment); in such way, a detector may be said to be coupled to a flow (or substance), such as an eluate.

It is of note that some methods, especially analytical methods, may involve continuous flow systems. As such, at least one liquid may be flowing from the vessel, under pressures that are greater than ambient (e.g., pump pressure effected by pump 32), at any time. Although indeed processing embodiments may involve continuous flow, typically, but not necessarily, a solution processing method, and the batch type vat that may find use in such method, will not be continuously flowing; instead, such processing may involve only gravity flow, and the outlet from the vessel may indeed be closed at least some time during operation. Any type of system may be internally pressurized (especially continuous flow systems); pressures may be any that do not break system components and provide acceptable (e.g., sufficiently accurate when analyzing) results. Internal pressures used in the experimental testing includes 50-500 psi, but highly pressurized systems (e.g., up to 12,000 psi) may also be used. Such systems (or indeed other systems), whether continuous flow or not, may include a solvent selection valve 29. Of note also is the fact that any change in flow (e.g., via valves or otherwise, whether from one solvent to a different solvent or otherwise) may be step-wise, or instead be gradual. A gradual change will change solvents over a longer period of time than does a step-wise change (with only practical limitations on the maximum length of time that can be taken for a gradual change). Of general note is the fact that U.S. Pat. No. 7,875,464, incorporated herein, may act to provide additional details regarding, e.g., the fractionation of asphaltenes via a successive dissolution protocol, including data for specific successive asphaltene dissolution experiments, experimental setup, inter alia.

Figure 1:
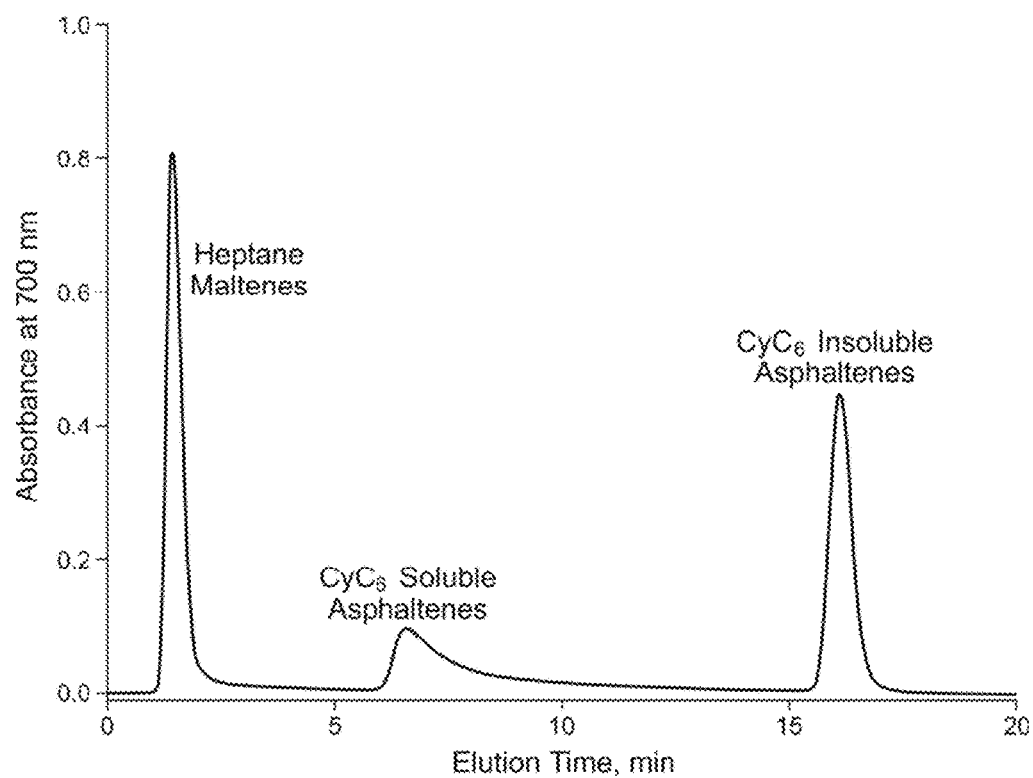
FIG. 1 shows an Asphaltene Separation Profile for 10 mg Redwater, B.C. Residuum on 160×8.0 mm PTFE Column, 700 nm Absorbance Detector. Gradient: 0 min. Heptane, 2 min. Cyclohexane, 15 min. Toluene:methanol (98:2), 40 min. Heptane; 3.0 mL/min.
Figure 2:
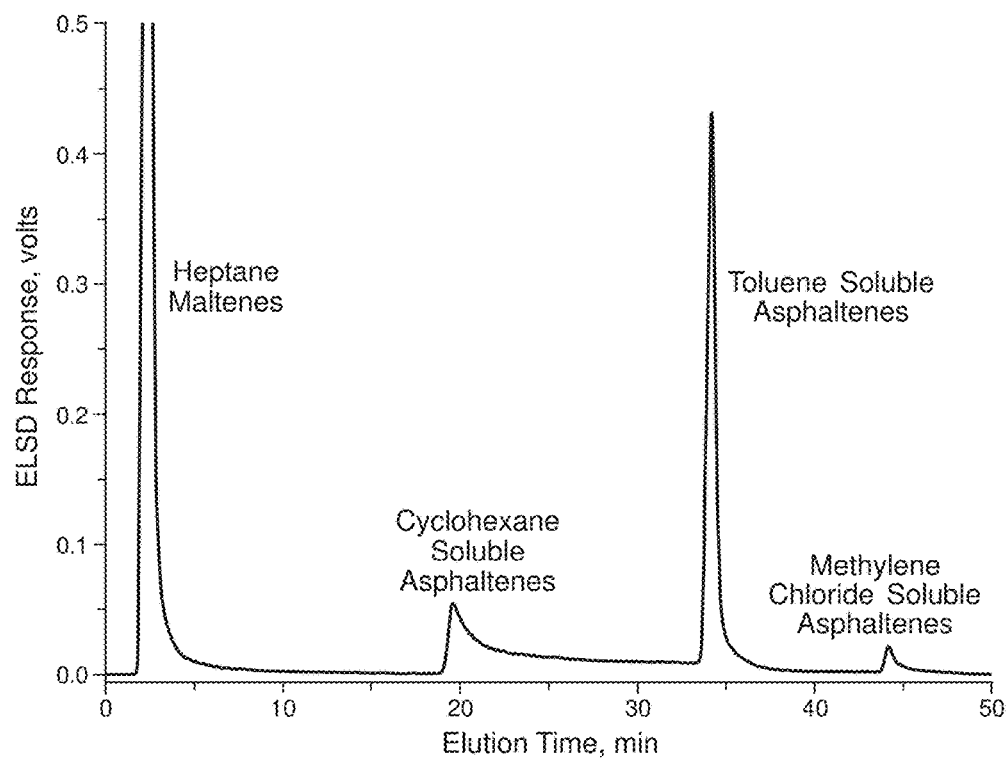
FIG. 2 shows an Asphaltene Separation of 2 mg (10 uL) Unpyrolyzed Boscan Residuum in Methylene Chloride on 250 mm×10 mm PTFE Column, ELSD Detector. Gradient.

Information regarding the asphalene fractions, whether stemming from a separation profile 21 (e.g., peak values, such as peak heights, peak sharpness, and peak areas; ratios thereof; times until, between or during elution(s), absence of peaks, sharpness of peaks, etc.) or from other data, e.g., the compositional makeup of maltenes derived from a SEC based analysis, can be, if required, mathematically manipulated (in a manner well known in the art) to provide even more information, thereby enabling even greater control over all types of operations. Reference is made specifically to FIGS. 1 and 2.

Asphaltene Determinator+SEC: The microstructure and colloidal models of asphalt structuring have gained general acceptance in recent years due to a preponderance of data (Lesueur 2009, Le Guern 2010). Size exclusion chromatography separations (SEC) performed at WRI that separated asphalt into one fraction of associated components and a second fraction of non-associating components were among early evidence supporting these models (Branthaver et al. 1993). Several permutations of SEC separations of asphalt involving a variety of separation conditions exist in the literature (Altgelt and Hirsch 1970; Haley 1975; Brule 1983, Pribanic 1989, Jennings 1992, Kim 1993; Bishara and McReynolds 1992; Schabron et al. 2001; Wahhab et al. 1999), including methods for quantification of polymer and monitoring polymer degradation with oxidative aging (McCann et al. 2008, Dreessen et al. 2010). These methods either rely on the manual collection and weighing of the elution material at designated times or a detector, typically differential refractive index (RI), to correlate specific asphalt material with hydrodynamic volume and, consequently, molecular weight. The former method is typically used if further analysis of the material is needed. The latter type of separation, often referred to as analytical scale SEC, is more rapid for higher throughput and is generally more precise.

A major drawback in using an RI detector for quantification of asphalt molecular weights from SEC separations is that different types of molecules give different changes in RI for a particular solvent. For example, waxes within an asphalt binder show a negative change in RI, and more polar asphaltene type molecules give a very positive change in RI. Aromatics and weakly polar molecules are somewhere in the middle of this polarity spectrum and show a moderately positive change in RI. As an alternative, an evaporative light scattering (ELS) detector can be used that responds more uniformly across sample types (Carbognani, 1997).

The molecular weight of the unassociated non-polar fractions can have an important effect on asphalt viscosity (Redelius 2015). Traditionally, using a column/solvent strength combination to separate asphalt into a polar/associated fraction and nonpolar/unassociated fraction has been effective at obtaining the average molecular weight of the non-polar asphalt portion (Le Guern 2010). An alternative approach to the above separation would be to separate the asphaltenes from the maltenes prior to running an SEC separation. This, new approach may give more accurate information on the molecular weight of the unassociated species.

In U.S. Pat. No. 7,875,464, a column housing a substantially chemically inert stationary phase (e.g., PTFE, as but one example) is used as a retention site for asphaltenes precipitated by a precipitant solvent such as heptane. After injection of the sample into an n-heptane mobile phase, the asphaltenes precipitate onto the PTFE column, and the maltenes proceed with the mobile phase as a first eluate.

A novel improvement addressed in this provisional patent is the addition of a second column (e.g., a SEC column, with a SEC stationary phase established therein) to provide detector-achieved measurement of the molecular weight of the maltenes (the heptane soluble compounds that elute from the PTFE column as the first eluate). A configuration that places a gel-permeation column (using GPC, also known as size exclusion chromatography, SEC) at a point after the PTFE column is disclosed in this application to enable measurement of the molecular weight or molecular size profiles of the maltenes (via a detector(s) configured to measure at least one response for the eluate from the SEC column, perhaps referred to herein as the second eluate). If desired, the precipitated asphaltenes retained within the substantially chemically inert stationary phase column can be dissolved, perhaps all at once with a strong material dissolving solvent, perhaps portion by portion using a successive dissolution procedure that involves material dissolving solvents of increasing strength. The dissolved asphaltenes thus elute from the inert stationary phase column as least a third eluate (a successive dissolution procedure would generate different additional eluates.

Gel permeation chromatography (also known as SEC) separates the components of asphalt by molecular size or volume. In GPC, the large components elute from the column first, while the smaller components elute later (although all are considered a second eluate, and part thereof). Conventional GPC of whole-sample asphalt, bitumen, and heavy oil samples that include asphaltenes has inherent problems due to the chemical tendencies of the asphaltenes to associate or agglomerate (or disassociate or disagglomerate) upon dilution as a function of solvent strength, temperature, and sample concentration. False high molecular weights of asphaltenes are often reported due to the chemical associations that are induced upon GPC analysis. The presence of the associated asphaltenes in the SEC profile adversely affects the ability of the chromatographic technique to accurately measure the molecular size or weight distributions of the sample. Since the presence and intensity of associated asphaltene species are induced artifacts or effects of the SEC parameters and separation conditions itself, it does not always provide an accurate measurement of the molecular weight distribution of the whole sample.

The present invention overcomes the asphaltene association problem by first precipitating out the asphaltenes using the PTFE column. In this fashion, the maltenes only may be directed by elution into a GPC/SEC column with detection including, but not limited to, IR, FTIR, NIR, MWD, VWD, DAD/PDA, FD, RI, ELSD and intrinsic viscosity detection. Note that SEC is a broad term, and includes but is not limited to known techniques such as GPC, whether exclusion occurs based on size, molecular weight, mass, volume, etc.

The molecular weight ranges of an asphalt or bitumen play a significant role in the physical behavior of asphalts at low through high temperatures and at high through low frequency of mechanical applications. Therefore the ability to determine an asphalt, heavy oil, bitumen, or blends' molecular weight ranges through an improvement of the on-column precipitation technique would add significant applicability of the technique to more fully characterize asphalt (or hydrocarbonaceous material generally), troubleshoot problematic misbehaved asphalts, and predict how an asphalt/hydrocarbonaceous material will perform in the field at a variety of temperatures and frequencies of duty cycles.

In particular embodiments, some thing, e.g., an eluate (which may include a fraction, e.g., an asphaltene fraction), may be analyzed. This may involve the step of measuring at least one response (which includes perhaps first obtaining that response) for at least one of such thing(s), e.g., eluate, using at least one detector (where the flow/eluate to which a detector may be coupled may be indicated with an "eyeball" symbol). Measuring a response (e.g., a refractive index response, as but one of many possible responses) may include measuring a change in response and/or comparing that response to a standard response. Embodiments may further comprise the step of determining the amount of at least one analyte (e.g., a specific compound of interest) of at least one eluate or fraction (or other thing) based on (e.g., via the mathematical or other use of) said at least one response. As such, a detector established to measure a response for an eluate or fraction, e.g., can be mounted according to well-known methods so that it can "detect an analyte" (e.g., via measuring a response that varies depending on, e.g., an amount of that analyte) of that eluate/fraction. It is also of note that measuring a response for an eluate may include measuring a response for only part of that eluate.

FIG. 3 shows a setup based on a type of Asphaltene Determinator; the setup shown includes a SEC column after the (substantially chemically) inert stationary phase (26) column (27). It is of note that in certain embodiments where the focus is analysis of maltenes (which may elute, as a first eluate, with the precipitant solvent from the inert stationary phase column when the asphaltenes are precipitated therein) and it is not desired to analyze the precipitated asphaltenes, equipment dedicated to the analysis of the asphaltenes (e.g., 25, 29, 22) may be eliminated. FIG. 3 shows the (optional) equipment that if included, can analyze the precipitated asphaltenes as they are eluted (perhaps via a successive dissolution procedure that uses one or more material (e.g., asphaltene) dissolving solvents (of increasing strength) to dissolve the precipitated asphaltenes). If indeed material dissolving several solvents are used to analyze asphaltenes (indeed, 25 is intended to represent not only one but several solvents), they may be used to successively dissolve different portions of the asphaltenes precipitated in column 26; each solvent may result in an elution for which a detector (22) measurement can be made, thereby allowing, e.g., determination of the amount of asphaltenes soluble in the particular solvent. One sufficiently strong material dissolving solvent may be used to dissolve all asphaltenes where the goal is only removal of precipitated asphaltenes from column 27, or merely, e.g., to quantify the amount of total asphaltenes instead of fractions thereof.

As to the operation of the exemplary system of FIG. 3, first the precipitant solvent of 24 may be passed, along with a portion of the solution of interest (e.g., a hydrocarbonaceous material, whether itself dissolved in solvent first or not), along path 24' into inert stationary phase column 27 (note that valve 29 is set so that flow comes exclusively from 24). Asphaltenes of the (portion of the) hydrocarbon injected into 24' and column 26 precipitate and are held within column 27 via the inert stationary phase 26 (with no significant adsorption thereon). Valve 110 is set so that the first eluate (with maltenes therein, but virtually no or no asphaltenes therein) from the column 27 is directed to SEC column, and then analyzed via a detector configured for measurement of a response for eluate (perhaps referred to as a second eluate) from the column (note also optional detector between valve 110 and the SEC column). After flow 24' through the SEC column is sufficient to analyze the maltenes as desired, and if it is desired to remove or analyze the precipitated asphaltenes in column 27 (indeed, there will usually be a desire to at least remove those precipitated asphaltenes), then flow valve 29 may be switched to direct solvent flow from source 25 through the pump to column 27 (no additional hydrocarbons are entrained into the solvent flow at this time) along path 25'. That material dissolving solvent(s) then passes through column 27, dissolving at least a portion of the precipitated asphaltenes, generating at least a third eluate (and possibly at least one different additional eluate in the case of a successive dissolution procedure that involves the use of more than one material dissolving solvent). Valve 110 has been reset (from its previous position directing flow towards the SEC column along path 24') so that the eluate from column 27 proceeds up to detector 22 along path 25'. Again, if this is a successive dissolution procedure, solvent source 25, as a schematic representation of one or more material dissolving solvents, becomes a source of stronger solvent also (of course this would practically involve, e.g., switching solvents or a valve), allowing for dissolution of at least a portion of the remaining portion of the precipitated asphaltenes (flow still occurs along path 25') in at least one different additional eluate, typically repeating until a strong enough solvent has been passed through column 27 to dissolve and eliminate therefrom substantially all of the remaining precipitated asphaltenes. It is of note that valve 110 is schematic, and of general representation only, such that it also represents any other way of directing flow from column 27 (e.g., processor-controlled gating technology at the column outlet, etc.) It is also of note that detector 22 can be used not only to detect asphaltenic eluate (i.e., eluate from the inert stationary phase column 27 that contains dissolved asphaltenes, whether fractional or all asphaltenes), but also the eluate from the SEC column; such could be achieved with appropriate valving and flow direction that would be known to one of ordinary skill in the art). Indeed, use of detector 22 to analyze both the SEC eluate and the eluate from the inert column is consistent with the expressed meaning of the "eyeball" symbol, and FIG. 3; in such case, 22 would be a shared detector. 21 could possibly be used to display results of both detections, regardless of whether the same or different detectors are used.

The results of SEC analysis (e.g., via a SEC stationary phase (in a vessel) and a detector configured to measure at least one response for an eluate from that vessel) provide information for the various components' molecular size, weight, or volume for the sample that is input into that column (perhaps, e.g., as dissolved in a solvent such as heptane).

Note that vessels (e.g., columns) can be set in series, parallel, singularly, as multiples, arranged for precipitation, adsorption, size exclusion, etc. Embodiments of the inventive technology may feature, either alone or in combination, isocratic or gradient elution profiles, flow patterns, valves, step-wise or gradual (here defined as being not step-wise) changes to, e.g., the solvent at the pump, and/or gradual and continuous, inter alia. Material dissolving solvents may be carefully chosen to improve elution capability and for overcoming detector limitations; solvents even can be changed, and even mid-stream or mid-detection, or at other times, in order to gain additional information regarding, e.g., one or more analytes. Different detectors can be combined in any of several ways, as different combinations may demonstrate different sensitivities to various analyte(s). And, while certain detectors may be best suited for placement after certain vessel(s) (e.g., columns) to detect specific eluate(s), the inventive technology generally, in embodiments, includes the use of detectors placed at various locations to detect analytes of any of a variety of eluate(s). The same may be true for placement of certain vessels, e.g., a size exclusion chromatography column. Indeed, while it may be particularly useful (for detection of analytes in its eluate), to place a SEC column immediately after an inert stationary phase column, whether with valving therebetween or not, eluate from the SEC column may offer illuminating information (e.g., when eluate therefrom has a detector (e.g., RI detector) coupled thereto) regarding, e.g., mass/volumetric sizes of the various components of that eluate.

Note that, in keeping with terminology as used in certain priority applications, a mobile phase can be, e.g., a solvent mobile phase where it is "amended" to include a hydrocarbon, components thereof, or to be free of a hydrocarbon or components thereof. This would be understood by one of ordinary skill in the art, without its specific mention, however.

Applications of the inventive technology, in embodiments, include but are not limited to: any exemplary applications described elsewhere in this technology, and process control, process refining, refining generally, analysis/review/testing/investigation/formulation/production of catalysts, rejuvenators, REOB (refined engine oil bottoms), additives, modifiers, polymers, surface active agents, colloids, contaminants, etc., estimation/prediction of fouling, coking, sediment formation, etc. And generally, embodiments of the inventive technology may manifest in or as a dedicated platform that is specific to a targeted test or analysis, or as a more universal platform with capabilities to achieve a wider analytical scope.

Particular embodiments of the inventive technology may even have application in continuous or batch, scaled up operations. Indeed, particular embodiments may help to improve control such operations.

While much of the written description focuses on methods, the inventive technology also includes apparatus, e.g., including but not limited to those shown, perhaps schematically, in the figures. Components disclosed as having flow lines therebetween may be said to be in fluidic communication with each other. It is of note that as used herein, generally, the term substantially means within 5% of (e.g., substantially all means within 5% of "all").

The ability to include GPC/SEC may prove to be an especially reliable technique to discern the presence of relatively different molecular weight materials such as additives, re-refined engine oil bottoms (REOB), and bio-based additives and rejuvenators which can be added to offset or restore some of the physical and chemical properties of, e.g., stiff, brittle recycled asphalt materials. Some mostly-lower-molecular weight softeners, bio-additives, re-refined engine oil bottoms, rejuvenators might possibly be of sufficiently low molecular weight to prevent their detection using evaporative light scattering detection (ELSD). Therefore, detecting the lower molecular weight material as a measurable peak (that can be integrated electronically and compared to the asphalt portion) of a GPC separation is an advancement in detection and measurement capability.

Examples of the distinct advantage of the improved PTFE column-produced maltenes SEC technique are provided below.

FIG. 4 shows four comparisons of the same sample of asphaltenes that were analyzed using conventional SEC separation. As the concentration of the asphaltenes sample is increased, increased associations are induced and displayed by the refractive index detector response. The increased associations are evident as apparent increased molecular weights or sizes (i.e, a shift to lower elution volumes). The resulting molecular weight distribution is forced higher and higher, in spite of the fact that the asphaltenes are in fact the same sample for each analysis condition. Because these effects are an artifact or result of the separation parameters itself, the resulting molecular size measurements are not dependable. At highest concentrations, multiple molecular sizes are evident, which cause interference issues with obtaining a true molecular size measurement of the whole sample, of which asphaltenes are a component.

FIG. 5 shows an SEC profile in which an asphalt sample containing an additive or modifier known as REOB (re-refined engine oil bottoms, also known as VTAE, vacuum tower asphalt extenders) was analyzed using a second column (an SEC column) at a point after the PTFE column as described above. In this example, the asphaltenes were first precipitated on the PTFE column (with a substantially chemically inert stationary phase) using a precipitant solvent, and therefore excluded from subsequent SEC analysis. The maltenes (the unprecipitated portion of the sample) were eluted with the mobile phase from the PTFE column as a first eluate, and directed to the SEC column (the additional column of the separation scheme). The resulting separation profile in FIG. 5 shows, in order of the various flows of the eluate from the SEC (i.e., the second eluate), a relatively high molecular weight polyisobutylene component which is conventionally found in REOB from the original engine oil formulation, followed by the asphalt peak, followed by the injection solvent peak. It is of note, incidentally, that the terms "first", "second", etc., particularly as used with respect to eluates, do not necessarily mandate a corresponding temporal order (indeed, in certain applications, there may be intervening eluate(s) between the "first" and "second" nominated eluates), but instead are used merely to facilely identify them (e.g., the first eluate is of the maltenes from inert stationary phase column). This example demonstrates that REOB (either intentionally or unintentionally) added to an asphalt may be detected by the new technique using its polyisobutylene fingerprint identifier. It is doubtful that the separation results would be unequivocally conclusive if associated asphaltenes were present in this analysis, because the associated asphaltenes would interfere with the detection of the polyisobutylene. Associated species are found in the molecular size region of polyisobutylene, thus preventing the identification and quantitation of polyisobutylene. The detector used in the FIG. 5 example is refractive index detection (RID).

FIG. 6 shows that the novel SEC technique in which asphaltenes are precipitated from the maltenes, and the maltenes are analyzed by SEC, can be used for assessing whether or not an asphalt sample is a blend. FIG. 6 shows the added column SEC analysis of an asphalt sample that comprises a CA Valley base asphalt that has a lower molecular weight and an Alaska North Slope base asphalt that has a higher molecular weight. A bimodal separation has been achieved. The detector used in this example is also the RID.

The advantage of the new multi-dimensional SEC technique is evident when a conventional SEC separation of the blended asphalt is considered. FIG. 7 shows the same blended asphalt analyzed by SEC in which the asphaltenes have not been removed from the sample's SEC analysis. The association effects of the asphaltenes present in the separation can be misleading, leading an analyst to believe that the asphalt sample is a single binder showing asphaltenes associated at the higher molecular weight shoulder of an asphalt peak.

FIGS. 8 and 9 show that the novel SEC separation performed on de-asphaltened samples does not significantly change the performance of the resulting molecular weight measurement. FIG. 8 shows the same SHRP (Strategic Highway Research Program) AAM West Texas Intermediate (WTI) crude source sample shown in FIG. 7, except the asphaltenes have been removed by the prior precipitation step. Additionally, FIG. 9 shows a de-asphaltened SEC analysis of the same visbroken sample shown in FIG. 7. In the whole-sample conventional SEC-RID analysis provided in FIG. 7, note that the higher molecular weight AAM asphalt elutes before the visbroken asphalt, although, again, both are considered part of the same eluate (e.g., of a second eluate). This result is portrayed to show that the SEC of the deasphaltened maltenes produces the correct conclusion: the higher molecular weight AAM sample does in fact elute in a lower elution volume than the visbroken lower-molecular weight sample. Therefore, it is shown that precipitation of the asphaltenes from the portion analyzed by SEC does not adversely affect the performance of the SEC separation to provide suitable molecular weight results for the maltenes.

FIG. 10 shows the utility of the new SEC technique to be used in addition to (and not exclusive of) conventional SEC. FIG. 10 shows a Canadian asphalt (SHRP AAA). FIG. 11 shows the same sample version (SHRP AAE) that has been oxidized by air-blowing. Although air-blowing an asphalt is well-known to increase asphaltene concentration, a comparison of air-blown sample to the one that has not been air-blown shows that the deasphaltened maltenes do not show any significant differences in their molecular weight profiles. FIG. 12 shows the same two asphalts—before and after air blowing—by conventional SEC and how different the asphaltene contents are. Analyzing samples by both the conventional and novel SEC techniques can therefore be used to help elucidate whether an asphalt is air blown or a blend. Therefore it is show that the novel deasphaltened maltenes SEC technique can be used not only as an alternative to conventional SEC, but also as a complementary technique to provide additional information that conventional SEC cannot offer.

It is of note that the SEC based inventive technology disclosed herein is not necessarily limited to situations where asphaltenes are removed from an hydrocarbonaceous material via use of a precipitant solvent. Indeed, de-asphaltening (i.e., removing asphaltenes from the material, leaving, e.g., maltenes) can occur via other methods, e.g., gravimetrically. Of course, in such case, the inventive technology would not include the steps and equipment associated with the inert stationary phase column used as a retention site for the precipitated asphaltenes.

The results of the detection can be then analyzed using any chemometrics software or deconvolution methods and particularly these based on neural networks, partial least squares, principal component analysis or the ExpliFit multi linear regression software from WRI which is especially useful for applications where insufficient observations are available compared to the number of independent measurement variables available. Chemometric software can be used for the determination of mathematical relationships of the analytical results of the chemical measurements coming from the AD+SEC, and further for the determination of mathematical relationships between these analytical results and other chemical or physical measurements obtained independently.

It is of note that the inventive technology is not limited to method disclosed herein, but instead also includes apparatus that can perform such methods. As such, in at least one apparatus embodiment, the inventive technology comprises AD equipment (as disclosed herein, and in U.S. Pat. No. 7,875,464 (or indeed any of the priority applications and patents into which they have matured), in addition to a SEC column established downflow of an inert stationary phase, and at least one detector coupled to eluate from such column.

Applications: the inventive technology disclosed herein can be used to analyze all kinds of hydrocarbonaceous materials, including hydrocarbon mixtures and more particularly asphalt binder blends which are commonly used by the industry or currently under development. It is particularly appropriate for characterizing the chemical properties of oil (petroleum or non-petroleum derived), asphalts including natural asphalts, polymers, and additives including biomass origin materials, surface active agents, colloids, recycled and aged asphalts, and blends.

Asphalt blends can include but are not limited to any type of asphalt binder used for roofing, paving, sealing of any type of applications. The blends include but are not limited to:

Blends from refining bases (residues from straight run distillation, solvent deasphalting, airblowing, visbreaking, hydrotreating, and cracking, coking, or any conversion units).

Any of above blends further modified with any semi-compatible additives, including but not restricted to polymers and/or additives possibly used in combinations. Polymers can include, but with no restriction all kinds of polymers compatible in asphalt to some degree, including polybutadiene and hydroxy and carboxy-polybutadiene, rubbers, styrene copolymers such as SBS, SB, SBR, SEBS, SIS, polyolefins such as PE, PP, APP, polyisobutylene, EPDM, oxidized polyolefins, polyethylene copolymers such EVA, EBA, EMA, EGMA and terpolymers of the later ones. Additives comprise acids including phosphonic, phosphoric and polyphosphoric acids, carboxylic and sulfonic acids, including polycarboxylic acids, fatty acids, bases, amphoterics, esters, anhydrides, paraffins (such as but not limited to Fischer Tropsch paraffines), waxes, amines, fatty amines, amides, sulfur, sulfur derivatives, peroxides, phenols, antioxidants, peroxides, surfactants and salt derivatives, functionalized additives from biomass origins, functionalized additives with fatty, naphthenic or aromatic chains or substituents, organometallic salts. Any polymer can be combined with any additive.

Blends of any of the above with aged asphalts from recycled paving materials or recycled roofing materials with or without rejuvenators with chemical properties included in the description of above additives.

Blends of any of the above with oils from petroleum, coal or biomass origin, including lubricant oils, waste engine oils, refined engine oil bottoms, vegetable oils and waste vegetable oils.

Blends of any of the above at various degrees of aging, processing, reaction, or catalysis.

The knowledge obtained from this invention can be the full or partial, qualitative or semi quantitative composition of the blends. This can be particularly desirable for unknown blends.

This knowledge obtained from this invention can be then used to formulate, blend and mix more cost efficiently long-term performing asphalt materials, lubricants, greases, crude oils or any petroleum products, or more generally chemical products, including additives and polymers, making them easier and more cost effective to produce to analyze/detect/formulate/produce/quantify and survey in their long-term service life.

Embodiments of the inventive technology may be described by the following clauses:

1. A method comprising the steps of:
   providing a vessel having a substantially chemically inert stationary phase established therein and having at least one vessel inlet,
   inputting a precipitant solvent into said vessel;
   inputting a hydrocarbonaceous material into said vessel;
   intentionally precipitating asphaltenes within said vessel and in the presence of said substantially chemically inert stationary phase, wherein said substantially chemically inert stationary phase is substantially chemically inert relative to said asphaltenes such that substantially all said precipitated asphaltenes do not adsorb onto said substantially chemically inert stationary phase;
   generating a first eluate upon performing said step of intentionally precipitating said asphaltenes, said first eluate free of said precipitated asphaltenes and comprising maltenes;
   passing said first eluate through a size exclusion chromatography stationary phase;
   generating a second eluate, said second eluate output from a vessel housing said size exclusion chromatography stationary phase;
   measuring at least one response for said second eluate using at least one detector;
   inputting a material dissolving solvent into said vessel; and
   dissolving at least a portion of said precipitated asphaltenes with said material dissolving solvent to generate a third eluate.

2. A method as described in clause 1 wherein said at least one detector comprises a refractive index detector.

3. A method as described in clause 1 wherein said at least one detector comprises a detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

4. A method as described in clause 1 wherein and further comprising the step of determining the amount of at least one analyte of said second eluate based on said at least one response.

5. A method as described in clause 1 wherein said at least one response is used to generate information regarding an asphalt, REOB in an asphalt, whether an asphalt is airblown or a blend, additives in asphalts, modifiers in asphalts, polymer in asphalts, surfactants in asphalts, softeners in asphalts, and rejuvenators in asphalts.

6. A method as described in clause 1 wherein and further comprising the step of measuring at least one response for said third eluate using at least one additional detector.

7. A method as described in clause 6 wherein said step of dissolving at least a portion of said precipitated asphaltenes with said material dissolving solvent comprises the step of dissolving substantially all of said precipitated asphaltenes using a successive dissolution procedure where material dissolving solvents of increasing strength are successively passed over said precipitated asphaltenes, each dissolving a different portion thereof, and each generating a different additional eluate.

8. A method as described in clause 7 and further comprising the step of measuring at least one response for said different additional eluates using said at least one additional detector.

9. A method as described in clause 8 wherein said at least one additional detector comprises a detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

10. A method as described in clause 7 wherein said step of using a successive dissolution procedure where material dissolving solvents of increasing strength are successively passed over said precipitated asphaltenes comprises the step of step-wise changing from one of said material dissolving solvent to the next.

11. A method as described in clause 7 wherein said step of using a successive dissolution procedure where material dissolving solvents of increasing strength are successively passed over said precipitated asphaltenes comprises the step of gradually changing from one of said material dissolving solvent to the next.

12. A method as described in clause 1 wherein said steps of inputting a precipitant solvent into said vessel and inputting a hydrocarbonaceous material into said vessel occur substantially at the same time.

13. A method as described in clause 1 wherein said step of inputting a hydrocarbonaceous material into said vessel is performed by first establishing said hydrocarbonaceous material in said precipitant solvent 14. A method as described in clause 13 wherein step of establishing said hydrocarbonaceous material in said precipitant solvent further comprising the step of injecting said hydrocarbonaceous material in said precipitant solvent
15. A method as described in clause 13 wherein said hydrocarbonaceous material is dissolved in a solvent when established in said precipitant solvent
16. A method as described in clause 1 wherein said step of inputting a hydrocarbonaceous material into said vessel comprises the step of inputting a hydrocarbon sample into said vessel.
17. A method as described in clause 1 wherein each of said steps is started in the order in which it appears.
18. A method as described in clause 1 wherein said step of providing a vessel having a substantially chemically inert stationary phase established therein comprises the step of providing a vessel having established therein a stationary phase selected from the group of: oligomers of PTFE, polymers of PTFE, polyphenylene sulfide, fluorinated polymers, silicon polymer and PEEK.
19. A method as described in clause 1 wherein said step of providing a vessel having a substantially chemically inert stationary phase established therein comprises the step of providing a batch type vessel having a substantially chemically inert stationary phase established therein.
20. A method as described in clause 1 wherein said method is a method selected from the group consisting of coking onset estimation method, oil processing method; asphalt composition determination method; oil fractionating method, oil production method, pipeline fouling related method, hydrotreating, cracking method, catalyst performance method, sediment estimation method, distillation method, vacuum distillation method, atmospheric distillation method, visbreaking method, blending method, asphalt formation method, asphalt extraction method, air blowing method, solvent deasphaltening method, and asphaltene content of oil measurement method.
21. A method as described in clause 1 wherein said method is an automated method.
22. A refinery or apparatus in which the method of clause 1 is performed.
23. A refinery that processes hydrocarbons based on analysis results generated, at least in part, upon performance of the method of clause 1.
24. A product produced by a process that is based on analysis results generated, at least in part, upon performance of the method of clause 1.
25. Controlling, designing, or monitoring processing of, a hydrocarbon through use of information generated from the method of clause 1.
26. A method as described in clause 1 further comprising the step of determining a concentration of an asphaltene fraction of said hydrocarbonaceous material.
27. A method as described in clause 1 further comprising the step of generating a solubility profile of asphaltenes of said hydrocarbonaceous material.
28. A method as described in clause 1 further comprising the step of determining at least one solubility parameter for said hydrocarbonaceous material.
29. A method as described in clause 1 further comprising the step of determining at least one asphaltene stability parameter.
30. A method as described in clause 1 wherein said step of determining at least one asphaltene stability parameter comprises the step of determining a coking index.
31. A method as described in clause 1 further comprising the step of improving the efficiency of a distillation process by monitoring an asphaltene stability parameter.
32. A method as described in clause 1 wherein said step of improving the efficiency of a distillation process by monitoring an asphaltene stability parameter comprises the step of improving the efficiency of a distillation process by monitoring a coking index.
33. A method as described in clause 1 further comprising the step of reducing pipeline fouling in a refinery by a hydrocarbon being processed, in part through the use of information gained, at least in part, upon performance of the method of claim 1.

As can be easily understood from the foregoing, the basic concepts of the present invention may be embodied in a variety of ways. It involves both analyzing techniques as well as devices to accomplish the appropriate analysis. In this application, the analyzing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any acts of law, statutes, regulations, or rules mentioned in this application for patent; patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the analysis devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method comprising the steps of:
providing a vessel having a substantially chemically inert stationary phase established therein and having at least one vessel inlet, inputting a precipitant solvent into said vessel;
inputting a hydrocarbonaceous material into said vessel;
intentionally precipitating asphaltenes within said vessel and in the presence of said substantially chemically inert stationary phase, wherein said substantially chemically inert stationary phase is substantially chemically inert relative to said asphaltenes such that substantially all said precipitated asphaltenes do not adsorb onto said substantially chemically inert stationary phase;
generating a first eluate upon performing said step of intentionally precipitating said asphaltenes, said first eluate free of said precipitated asphaltenes and comprising maltenes;
passing said first eluate through a size exclusion chromatography stationary phase;
generating a second eluate, said second eluate output from a vessel housing said size exclusion chromatography stationary phase;
measuring at least one response for said second eluate using at least one detector;
inputting a material dissolving solvent into said vessel; and
dissolving at least a portion of said precipitated asphaltenes with said material dissolving solvent to generate a third eluate.

2. A method as described in claim 1 wherein said at least one detector comprises a refractive index detector.

3. A method as described in claim 1 wherein said at least one detector comprises a detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

4. A method as described in claim 1 wherein and further comprising the step of determining the amount of at least one analyte of said second eluate based on said at least one response.

5. A method as described in claim 1 wherein said at least one response is used to generate information regarding an asphalt, REOB in an asphalt, whether an asphalt is airblown or a blend, additives in asphalts, modifiers in asphalts, polymer in asphalts, surfactants in asphalts, softeners in asphalts, and rejuvenators in asphalts.

6. A method as described in claim 1 wherein and further comprising the step of measuring at least one response for said third eluate using at least one additional detector.

7. A method as described in claim 6 wherein said step of dissolving at least a portion of said precipitated asphaltenes with said material dissolving solvent comprises the step of dissolving substantially all of said precipitated asphaltenes using a successive dissolution procedure where material dissolving solvents of increasing strength are successively passed over said precipitated asphaltenes, each dissolving a different portion thereof, and each generating a different additional eluate.

8. A method as described in claim 7 and further comprising the step of measuring at least one response for said different additional eluates using said at least one additional detector.

9. A method as described in claim 8 wherein said at least one additional detector comprises a detector selected from the group consisting of: ELSD, mass spectrometer, optical absorbance detector, refractive index detector, ultraviolet detector, ultrasound detector, x-ray detector, conductivity detector, oxidation/reduction detector, polarimetry detector, atomic spectrometer, DAD, FD, FTIR, and fluorescence detector.

10. A method as described in claim 7 wherein said step of using a successive dissolution procedure where material dissolving solvents of increasing strength are successively passed over said precipitated asphaltenes comprises the step of step-wise changing from one of said material dissolving solvent to the next.

11. A method as described in claim 7 wherein said step of using a successive dissolution procedure where material dissolving solvents of increasing strength are successively passed over said precipitated asphaltenes comprises the step of gradually changing from one of said material dissolving solvent to the next.

12. A method as described in claim 11 further comprising the step measuring at least one response for said third eluate using at least one shared detector.

13. A method as described in claim 1 wherein said steps of inputting a precipitant solvent into said vessel and inputting a hydrocarbonaceous material into said vessel occur substantially at the same time.

14. A method as described in claim 1 wherein said step of inputting a hydrocarbonaceous material into said vessel is performed by first establishing said hydrocarbonaceous material in said precipitant solvent.

15. A method as described in claim 14 wherein step of establishing said hydrocarbonaceous material in said precipitant solvent further comprising the step of injecting said hydrocarbonaceous material in said precipitant solvent.

16. A method as described in claim 14 wherein said hydrocarbonaceous material is dissolved in a solvent when established in said precipitant solvent.

17. A method as described in claim 1 wherein said step of inputting a hydrocarbonaceous material into said vessel comprises the step of inputting a hydrocarbon sample into said vessel.

18. A method as described in claim 1 wherein each of said steps is started in the order in which it appears.

19. A method as described in claim 1 wherein said step of providing a vessel having a substantially chemically inert stationary phase established therein comprises the step of providing a vessel having established therein a stationary phase selected from the group of: oligomers of PTFE, polymers of PTFE, polyphenylene sulfide, fluorinated polymers, silicon polymer and PEEK.

20. A method as described in claim 1 wherein said step of providing a vessel having a substantially chemically inert stationary phase established therein comprises the step of providing a batch type vessel having a substantially chemically inert stationary phase established therein.

21. A method as described in claim 1 wherein said method is a method selected from the group consisting of coking onset estimation method, oil processing method; asphalt composition determination method; oil fractionating method, oil production method, pipeline fouling related method, hydrotreating, cracking method, catalyst performance method, sediment estimation method, distillation method, vacuum distillation method, atmospheric distillation method, visbreaking method, blending method, asphalt formation method, asphalt extraction method, air blowing method, solvent deasphaltening method, and asphaltene content of oil measurement method.

22. A method as described in claim 1 wherein said method is an automated method.

23. A refinery or apparatus in which the method of claim 1 is performed.

24. A refinery that processes hydrocarbons based on analysis results generated, at least in part, upon performance of the method of claim 1.

25. A product produced by a process that is based on analysis results generated, at least in part, upon performance of the method of claim 1.

26. Controlling, designing, or monitoring processing of, a hydrocarbon through use of information generated from the method of claim 1.

27. A method as described in claim 1 further comprising the step of determining a concentration of an asphaltene fraction of said hydrocarbonaceous material.

28. A method as described in claim 1 further comprising the step of generating a solubility profile of asphaltenes of said hydrocarbonaceous material.

29. A method as described in claim 1 further comprising the step of determining at least one solubility parameter for said hydrocarbonaceous material.

30. A method as described in claim 1 further comprising the step of determining at least one asphaltene stability parameter.

31. A method as described in claim 1 wherein said step of determining at least one asphaltene stability parameter comprises the step of determining a coking index.

32. A method as described in claim 1 further comprising the step of improving the efficiency of a distillation process by monitoring an asphaltene stability parameter.

33. A method as described in claim 1 wherein said step of improving the efficiency of a distillation process by monitoring an asphaltene stability parameter comprises the step of improving the efficiency of a distillation process by monitoring a coking index.

34. A method as described in claim 1 further comprising the step of reducing pipeline fouling in a refinery by a hydrocarbon being processed, in part through the use of information gained, at least in part, upon performance of the method of claim 1.

* * * * *